US010779904B2

(12) United States Patent
Ransbury et al.

(10) Patent No.: US 10,779,904 B2
(45) Date of Patent: Sep. 22, 2020

(54) SYSTEMS AND METHODS FOR LESION FORMATION AND ASSESSMENT

(71) Applicant: 460MEDICAL, INC., Cambridge, MA (US)

(72) Inventors: Terrance J. Ransbury, Chapel Hill, NC (US); Kenneth C. Armstrong, Cary, NC (US); Omar Amirana, Cambridge, MA (US); Cinnamon Larson, Carrboro, NC (US)

(73) Assignee: 460Medical, Inc., Cambridge, MA (US)

( * ) Notice: Subject to any disclaimer, the term of this patent is extended or adjusted under 35 U.S.C. 154(b) by 1179 days.

(21) Appl. No.: 14/919,004

(22) Filed: Oct. 21, 2015

(65) Prior Publication Data

US 2017/0014202 A1    Jan. 19, 2017

Related U.S. Application Data

(60) Provisional application No. 62/194,276, filed on Jul. 19, 2015.

(51) Int. Cl.
*A61B 90/30* (2016.01)
*A61B 18/14* (2006.01)
(Continued)

(52) U.S. Cl.
CPC ........ *A61B 90/30* (2016.02); *A61B 17/00234* (2013.01); *A61B 18/02* (2013.01);
(Continued)

(58) Field of Classification Search
CPC ....... A61B 90/30; A61B 90/37; A61B 90/361; A61B 17/00234; A61B 18/06; A61B 18/02; A61B 18/1492; A61B 18/1815; A61B 18/24; A61B 18/1206; A61B 2034/2051; A61B 2018/0066; A61B 2018/00577;
(Continued)

(56) References Cited

U.S. PATENT DOCUMENTS 4,619,247 A    10/1986  Inoue et al.
5,074,306 A    12/1991  Green et al.
(Continued)

FOREIGN PATENT DOCUMENTS

CN    1289239    3/2001
CN    1764419    4/2006
(Continued)

OTHER PUBLICATIONS

PCT International Search Report dated Dec. 8, 2016 for PCT/US2016/042891.
(Continued)

*Primary Examiner* — Peter Luong
(74) *Attorney, Agent, or Firm* — Greenberg Traurig, LLP; David J. Dykeman; Roman Fayerberg

(57) ABSTRACT

Catheter for visualizing ablated tissue comprises a catheter body; a distal tip positioned at a distal end of the catheter body, the distal tip defining a illumination cavity, the distal tip having one or more openings for exchange of light energy between the illumination cavity and tissue; a light directing member disposed within the illumination cavity, the light directing member being configured to split light energy received from a light source into multiple beams and to such beams to the tissue through the corresponding more openings in the distal tip.

22 Claims, 9 Drawing Sheets

(51) Int. Cl.
  *A61B 18/02* (2006.01)
  *A61B 18/06* (2006.01)
  *A61B 90/00* (2016.01)
  *A61B 17/00* (2006.01)
  *A61B 18/24* (2006.01)
  *A61B 18/18* (2006.01)
  *A61B 18/00* (2006.01)
  *A61B 18/12* (2006.01)
  *A61N 7/00* (2006.01)
  *A61B 34/20* (2016.01)

(52) U.S. Cl.
  CPC .......... *A61B 18/06* (2013.01); *A61B 18/1492* (2013.01); *A61B 90/361* (2016.02); *A61B 90/37* (2016.02); *A61B 18/1206* (2013.01); *A61B 18/1815* (2013.01); *A61B 18/24* (2013.01); *A61B 2017/00057* (2013.01); *A61B 2017/00061* (2013.01); *A61B 2018/0066* (2013.01); *A61B 2018/00351* (2013.01); *A61B 2018/00357* (2013.01); *A61B 2018/00363* (2013.01); *A61B 2018/00577* (2013.01); *A61B 2018/00982* (2013.01); *A61B 2018/00994* (2013.01); *A61B 2018/0212* (2013.01); *A61B 2018/1861* (2013.01); *A61B 2034/2051* (2016.02); *A61B 2090/306* (2016.02); *A61B 2090/3614* (2016.02); *A61B 2090/376* (2016.02); *A61B 2218/002* (2013.01); *A61N 7/00* (2013.01)

(58) Field of Classification Search
  CPC ........... A61B 2018/00982; A61B 2018/00363; A61B 2018/00357; A61B 2018/00351; A61B 2018/1861; A61B 2018/00994; A61B 2018/0212; A61B 2017/00061; A61B 2017/00057; A61B 2218/002; A61B 2090/376; A61B 2090/3614; A61B 2090/306; A61N 7/00
  See application file for complete search history.

(56) References Cited

U.S. PATENT DOCUMENTS

| | | | |
|---|---|---|---|
| 5,187,572 | A | 2/1993 | Nakamura et al. |
| 5,350,375 | A | 9/1994 | Deckelbaum et al. |
| 5,419,323 | A | 5/1995 | Kittrell et al. |
| 5,421,337 | A | 6/1995 | Richards-Kortum et al. |
| 5,507,287 | A | 4/1996 | Palcic et al. |
| 5,540,681 | A | 7/1996 | Strul et al. |
| 5,590,660 | A | 1/1997 | MacAulay et al. |
| 5,657,760 | A | 8/1997 | Ying et al. |
| 5,713,364 | A | 2/1998 | DeBaryshe et al. |
| 5,749,830 | A | 5/1998 | Kaneko et al. |
| 5,833,688 | A | 11/1998 | Sieben et al. |
| 5,885,258 | A | 3/1999 | Sachdeva et al. |
| 5,904,651 | A | 5/1999 | Swanson et al. |
| 5,954,665 | A | 9/1999 | Ben Haim |
| 6,064,069 | A | 5/2000 | Nakano et al. |
| 6,112,123 | A | 8/2000 | Kelleher et al. |
| 6,124,597 | A | 9/2000 | Shehada et al. |
| 6,174,291 | B1 | 1/2001 | McMahon et al. |
| 6,178,346 | B1 | 1/2001 | Amundson et al. |
| 6,197,021 | B1 | 3/2001 | Panescu et al. |
| 6,208,886 | B1 | 3/2001 | Alfano et al. |
| 6,217,573 | B1 | 4/2001 | Webster et al. |
| 6,219,566 | B1 | 4/2001 | Weersink et al. |
| 6,251,107 | B1 | 6/2001 | Schaer |
| 6,289,236 | B1 | 9/2001 | Koenig et al. |
| 6,309,352 | B1 | 10/2001 | Oraevsky et al. |
| 6,343,228 | B1 | 1/2002 | Qu |
| 6,423,055 | B1 | 7/2002 | Farr et al. |
| 6,423,057 | B1 | 7/2002 | He et al. |
| 6,450,971 | B1 | 9/2002 | Andrus et al. |
| 6,516,217 | B1 | 2/2003 | Tsujita |
| 6,522,913 | B2 | 2/2003 | Swanson et al. |
| 6,542,767 | B1 | 4/2003 | McNichols et al. |
| 6,572,609 | B1 | 6/2003 | Farr et al. |
| 6,584,360 | B2 | 6/2003 | Francischelli et al. |
| 6,626,900 | B1 | 9/2003 | Sinofsky et al. |
| 6,648,883 | B2 | 11/2003 | Francischelli et al. |
| 6,658,279 | B2 | 12/2003 | Swanson et al. |
| 6,663,622 | B1 | 12/2003 | Foley et al. |
| 6,663,627 | B2 | 12/2003 | Francischelli et al. |
| 6,671,535 | B1 | 12/2003 | McNichols et al. |
| 6,697,657 | B1 | 2/2004 | Shehada et al. |
| 6,706,038 | B2 | 3/2004 | Francischelli et al. |
| 6,716,196 | B2 | 4/2004 | Lesh et al. |
| 6,743,225 | B2 | 6/2004 | Sanchez et al. |
| 6,746,401 | B2 | 6/2004 | Panescu |
| 6,761,716 | B2 | 7/2004 | Kadhiresan et al. |
| 6,825,928 | B2 | 11/2004 | Liu et al. |
| 6,936,047 | B2 | 8/2005 | Nasab et al. |
| 6,937,885 | B1 | 8/2005 | Lewis et al. |
| 6,942,657 | B2 | 9/2005 | Sinofsky et al. |
| 6,953,457 | B2 | 10/2005 | Farr et al. |
| 6,974,454 | B2 | 12/2005 | Hooven |
| 6,975,898 | B2 | 12/2005 | Seibel |
| 6,975,899 | B2 | 12/2005 | Faupel et al. |
| 6,979,290 | B2 | 12/2005 | Mourlas et al. |
| 6,989,010 | B2 | 1/2006 | Francischelli et al. |
| 7,001,383 | B2 | 2/2006 | Keidar |
| 7,029,470 | B2 | 4/2006 | Francischelli et al. |
| 7,047,068 | B2 | 5/2006 | Haissaguerre |
| 7,130,672 | B2 | 10/2006 | Pewzner et al. |
| 7,192,427 | B2 | 3/2007 | Chapelon et al. |
| 7,207,984 | B2 | 4/2007 | Fan et al. |
| 7,232,437 | B2 | 6/2007 | Berman et al. |
| 7,235,045 | B2 | 6/2007 | Wang et al. |
| 7,250,048 | B2 | 7/2007 | Francischelli et al. |
| 7,252,664 | B2 | 8/2007 | Nasab et al. |
| 7,255,695 | B2 | 8/2007 | Falwell et al. |
| 7,289,205 | B2 | 10/2007 | Yaroslavsky et al. |
| 7,306,593 | B2 | 12/2007 | Keidar et al. |
| 7,338,485 | B2 | 3/2008 | Brucker et al. |
| 7,357,796 | B2 | 4/2008 | Farr et al. |
| 7,367,944 | B2 | 5/2008 | Rosemberg et al. |
| 7,367,972 | B2 | 5/2008 | Francischelli et al. |
| 7,497,858 | B2 | 3/2009 | Chapelon et al. |
| 7,527,625 | B2 | 5/2009 | Knight et al. |
| 7,534,204 | B2 | 5/2009 | Starksen et al. |
| 7,539,530 | B2 | 5/2009 | Caplan et al. |
| 7,587,236 | B2 | 9/2009 | Demos et al. |
| 7,591,816 | B2 | 9/2009 | Wang et al. |
| 7,596,404 | B2 | 9/2009 | Maier et al. |
| 7,598,088 | B2 | 10/2009 | Balas |
| 7,640,046 | B2 | 12/2009 | Pastore |
| 7,662,152 | B2 | 2/2010 | Sharareh et al. |
| 7,681,579 | B2 | 3/2010 | Schwartz |
| 7,727,229 | B2 | 6/2010 | He et al. |
| 7,727,231 | B2 | 6/2010 | Swanson |
| 7,729,750 | B2 | 6/2010 | Tromberg et al. |
| 7,766,907 | B2 | 8/2010 | Dando et al. |
| 7,776,033 | B2 | 8/2010 | Swanson |
| 7,822,460 | B2 | 10/2010 | Halperin et al. |
| 7,824,397 | B2 | 11/2010 | McAuley |
| 7,824,399 | B2 | 11/2010 | Francischelli et al. |
| 7,837,676 | B2 | 11/2010 | Sinelnikov et al. |
| 7,846,157 | B2 | 12/2010 | Kozel |
| 7,862,561 | B2 | 1/2011 | Swanson et al. |
| 7,877,128 | B2 | 1/2011 | Schwartz |
| 7,918,850 | B2 | 4/2011 | Govari et al. |
| 7,930,016 | B1 | 4/2011 | Saadat |
| 7,942,871 | B2 | 5/2011 | Thapliyal et al. |
| 7,950,397 | B2 | 5/2011 | Thapliyal et al. |
| 7,974,683 | B2 | 7/2011 | Balas et al. |
| 7,976,537 | B2 | 7/2011 | Lieber et al. |
| 7,979,107 | B2 | 7/2011 | Lin et al. |
| 7,996,078 | B2 | 8/2011 | Paul et al. |
| 8,007,433 | B2 | 8/2011 | Iketani |
| 8,024,027 | B2 | 9/2011 | Freeman et al. |
| 8,025,661 | B2 | 9/2011 | Arnold et al. |

(56) References Cited

U.S. PATENT DOCUMENTS

| | | |
|---|---|---|
| 8,050,746 B2 | 11/2011 | Saadat et al. |
| 8,078,266 B2 | 12/2011 | Saadat et al. |
| 8,123,742 B2 | 2/2012 | Berger |
| 8,123,745 B2 | 2/2012 | Beeckler et al. |
| 8,129,105 B2 | 3/2012 | Zuckerman |
| 8,131,350 B2 | 3/2012 | Saadat et al. |
| 8,137,333 B2 | 3/2012 | Saadat et al. |
| 8,144,966 B2 | 3/2012 | Provenzano et al. |
| 8,146,603 B2 | 4/2012 | Thapliyal et al. |
| 8,147,484 B2 | 4/2012 | Lieber et al. |
| 8,152,795 B2 | 4/2012 | Farr et al. |
| 8,160,680 B2 | 4/2012 | Boyden et al. |
| 8,175,688 B2 | 5/2012 | Lewis et al. |
| 8,180,436 B2 | 5/2012 | Boyden et al. |
| 8,188,446 B2 | 5/2012 | Ohno |
| 8,195,271 B2 | 6/2012 | Rahn |
| 8,203,709 B2 | 6/2012 | Ishii |
| 8,219,183 B2 | 7/2012 | Mashke et al. |
| 8,221,310 B2 | 7/2012 | Saadat et al. |
| 8,235,985 B2 | 8/2012 | Saadat et al. |
| 8,241,272 B2 | 8/2012 | Arnold et al. |
| 8,267,926 B2 | 9/2012 | Paul et al. |
| 8,277,444 B2 | 10/2012 | Arnold et al. |
| 8,298,227 B2 | 10/2012 | Leo et al. |
| 8,309,346 B2 | 11/2012 | Zuckerman |
| 8,317,783 B2 | 11/2012 | Cao et al. |
| 8,333,012 B2 | 12/2012 | Rothe et al. |
| 8,353,907 B2 | 1/2013 | Winkler et al. |
| 8,357,149 B2 | 1/2013 | Govan et al. |
| 8,366,705 B2 | 2/2013 | Arnold et al. |
| 8,369,922 B2 | 2/2013 | Paul et al. |
| 8,374,682 B2 | 2/2013 | Freeman et al. |
| 8,382,750 B2 | 2/2013 | Brannan |
| 8,403,925 B2 | 3/2013 | Miller et al. |
| 8,414,508 B2 | 4/2013 | Thapliyal et al. |
| 8,417,321 B2 | 4/2013 | Saadat et al. |
| 8,417,323 B2 | 4/2013 | Uzunbajakava et al. |
| 8,419,613 B2 | 4/2013 | Saadat et al. |
| 8,435,232 B2 | 5/2013 | Aeby et al. |
| 8,444,639 B2 | 5/2013 | Arnold et al. |
| 8,460,285 B2 | 6/2013 | Wang et al. |
| 8,463,366 B2 | 6/2013 | Freeman et al. |
| 8,500,730 B2 | 8/2013 | Lee et al. |
| 8,504,132 B2 | 8/2013 | Friedman et al. |
| 8,511,317 B2 | 8/2013 | Thapliyal et al. |
| 8,540,704 B2 | 9/2013 | Melsky et al. |
| 8,548,567 B2 | 10/2013 | Maschke et al. |
| 8,556,892 B2 | 10/2013 | Hong et al. |
| 8,583,220 B2 | 11/2013 | Schwartz |
| 8,603,084 B2 | 12/2013 | Fish et al. |
| 8,607,800 B2 | 12/2013 | Thapliyal et al. |
| 8,628,520 B2 | 1/2014 | Sharareh et al. |
| 8,641,705 B2 | 2/2014 | Leo et al. |
| 8,641,706 B2 | 2/2014 | Lieber et al. |
| 8,690,758 B2 | 4/2014 | Matsumoto |
| 8,702,690 B2 | 4/2014 | Paul et al. |
| 8,709,008 B2 | 4/2014 | Willis et al. |
| 8,728,077 B2 | 5/2014 | Paul et al. |
| 8,755,860 B2 | 6/2014 | Paul et al. |
| 8,774,906 B2 | 7/2014 | Harks et al. |
| 8,808,281 B2 | 8/2014 | Emmons et al. |
| 8,849,380 B2 | 9/2014 | Patwardhan |
| 8,858,495 B2 | 10/2014 | Tegg et al. |
| 8,876,817 B2 | 11/2014 | Avitall et al. |
| 8,882,697 B2 | 11/2014 | Celermajer et al. |
| 8,894,589 B2 | 11/2014 | Leo et al. |
| 8,894,641 B2 | 11/2014 | Brannan |
| 8,900,219 B2 | 12/2014 | Sinofsky et al. |
| 8,900,225 B2 | 12/2014 | Bar-Tal et al. |
| 8,900,228 B2 | 12/2014 | Grunewald et al. |
| 8,900,229 B2 | 12/2014 | Govari et al. |
| 8,906,011 B2 | 12/2014 | Gelbart et al. |
| 8,915,878 B2 | 12/2014 | Winkler et al. |
| 8,923,959 B2 | 12/2014 | Boveja et al. |
| 8,926,604 B2 | 1/2015 | Govari et al. |
| 8,929,973 B1 | 1/2015 | Webb et al. |
| 8,948,851 B2 | 2/2015 | Leblond et al. |
| 8,951,247 B2 | 2/2015 | Ding et al. |
| 8,986,292 B2 | 3/2015 | Sliwa et al. |
| 8,986,298 B2 | 3/2015 | Lee et al. |
| 8,998,890 B2 | 4/2015 | Paul et al. |
| 8,998,892 B2 | 4/2015 | Winkler et al. |
| 8,998,893 B2 | 4/2015 | Avitall |
| 9,008,746 B2 | 4/2015 | Pastore et al. |
| 9,014,789 B2 | 4/2015 | Mercader et al. |
| 9,084,611 B2 | 7/2015 | Amirana et al. |
| 9,220,411 B2 | 12/2015 | Hillman |
| 9,233,241 B2 | 1/2016 | Long |
| 9,277,865 B2 | 3/2016 | Yamaguchi et al. |
| 10,076,238 B2 | 9/2018 | Amirana et al. |
| 10,143,517 B2 | 12/2018 | Ransbury et al. |
| 10,568,535 B2 | 2/2020 | Roberts et al. |
| 2002/0042556 A1 | 4/2002 | Sugimoto et al. |
| 2002/0123666 A1 | 9/2002 | Matsumoto |
| 2002/0143326 A1 | 10/2002 | Foley et al. |
| 2003/0028188 A1 | 2/2003 | Paddock et al. |
| 2003/0120142 A1 | 6/2003 | Dubuc et al. |
| 2003/0120144 A1 | 6/2003 | Grabek et al. |
| 2003/0208252 A1 | 11/2003 | O'Boyle et al. |
| 2004/0073206 A1 | 4/2004 | Foley et al. |
| 2004/0092806 A1 | 5/2004 | Sagon et al. |
| 2004/0097788 A1 | 5/2004 | Mourlas et al. |
| 2004/0138656 A1 | 7/2004 | Francischelli et al. |
| 2004/0187875 A1 | 9/2004 | He et al. |
| 2004/0215310 A1 | 10/2004 | Amirana |
| 2004/0267326 A1 | 12/2004 | Ocel et al. |
| 2005/0014995 A1 | 1/2005 | Amundson et al. |
| 2005/0043637 A1 | 2/2005 | Caplan et al. |
| 2005/0075629 A1 | 4/2005 | Chapelon et al. |
| 2005/0119523 A1 | 6/2005 | Starksen et al. |
| 2005/0197530 A1 | 9/2005 | Wallace et al. |
| 2005/0197623 A1 | 9/2005 | Leeflang et al. |
| 2005/0215899 A1 | 9/2005 | Trahey et al. |
| 2005/0228452 A1 | 10/2005 | Mourlas et al. |
| 2005/0251125 A1 | 11/2005 | Pless et al. |
| 2005/0283195 A1 | 12/2005 | Pastore et al. |
| 2006/0009756 A1 | 1/2006 | Francischelli et al. |
| 2006/0013454 A1 | 1/2006 | Flewelling et al. |
| 2006/0025760 A1 | 2/2006 | Podhajsky |
| 2006/0089636 A1 | 4/2006 | Christopherson et al. |
| 2006/0122587 A1 | 6/2006 | Sharareh |
| 2006/0184048 A1 | 8/2006 | Saadat |
| 2006/0229515 A1 | 10/2006 | Sharareh et al. |
| 2006/0229594 A1 | 10/2006 | Francischelli et al. |
| 2007/0015964 A1 | 1/2007 | Eversull et al. |
| 2007/0016079 A1 | 1/2007 | Freeman et al. |
| 2007/0016130 A1 | 1/2007 | Leeflang et al. |
| 2007/0038126 A1 | 2/2007 | Pyle et al. |
| 2007/0049827 A1 | 3/2007 | Donaldson et al. |
| 2007/0083217 A1 | 4/2007 | Eversull et al. |
| 2007/0167828 A1 | 7/2007 | Saadat |
| 2007/0185479 A1 | 8/2007 | Lau |
| 2007/0225697 A1 | 9/2007 | Shroff et al. |
| 2007/0270717 A1 | 11/2007 | Tang et al. |
| 2007/0270789 A1 | 11/2007 | Berger |
| 2007/0270792 A1 | 11/2007 | Hennemann et al. |
| 2007/0270795 A1 | 11/2007 | Francischelli et al. |
| 2007/0276259 A1 | 11/2007 | Okawa et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015569 A1 | 1/2008 | Saadat et al. |
| 2008/0033241 A1 | 2/2008 | Peh et al. |
| 2008/0058650 A1 | 3/2008 | Saadat et al. |
| 2008/0058785 A1 | 3/2008 | Boyden et al. |
| 2008/0058786 A1 | 3/2008 | Boyden et al. |
| 2008/0097476 A1 | 4/2008 | Peh et al. |
| 2008/0101677 A1 | 5/2008 | Mashke et al. |
| 2008/0103355 A1 | 5/2008 | Boyden et al. |
| 2008/0119694 A1 | 5/2008 | Lee |
| 2008/0154257 A1 | 6/2008 | Sharareh et al. |
| 2008/0172049 A1 | 7/2008 | Bredno et al. |
| 2008/0183036 A1 | 7/2008 | Saadat et al. |
| 2008/0212867 A1 | 9/2008 | Provenzano et al. |

(56) References Cited

U.S. PATENT DOCUMENTS

| | | |
|---|---|---|
| 2008/0214889 A1 | 9/2008 | Saadat et al. |
| 2008/0221448 A1 | 9/2008 | Khuri-Yakub et al. |
| 2008/0228032 A1 | 9/2008 | Starksen et al. |
| 2008/0228079 A1 | 9/2008 | Donaldson et al. |
| 2008/0243214 A1 | 10/2008 | Koblish |
| 2008/0275300 A1 | 11/2008 | Rothe et al. |
| 2008/0281293 A1 | 11/2008 | Peh et al. |
| 2008/0300589 A1 | 12/2008 | Paul et al. |
| 2009/0012367 A1 | 1/2009 | Chin et al. |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076373 A1 | 3/2009 | Maschke |
| 2009/0076375 A1 | 3/2009 | Maschke |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0204069 A1 | 8/2009 | Hirszowicz et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0281541 A1 | 11/2009 | Ibrahim et al. |
| 2009/0292211 A1 | 11/2009 | Lin et al. |
| 2009/0299354 A1 | 12/2009 | Melsky et al. |
| 2009/0299363 A1 | 12/2009 | Saadat et al. |
| 2009/0306643 A1 | 12/2009 | Pappone et al. |
| 2010/0022832 A1 | 1/2010 | Makiyama |
| 2010/0041986 A1 | 2/2010 | Nguyen et al. |
| 2010/0081127 A1 | 4/2010 | Maier et al. |
| 2010/0081948 A1 | 4/2010 | Pastore et al. |
| 2010/0084563 A1 | 4/2010 | Ohno |
| 2010/0114094 A1 | 5/2010 | Thapliyal et al. |
| 2010/0130836 A1 | 5/2010 | Malchano et al. |
| 2010/0152728 A1 | 6/2010 | Park et al. |
| 2010/0198065 A1 | 8/2010 | Thapliyal et al. |
| 2010/0204544 A1 | 8/2010 | Takei |
| 2010/0204561 A1 | 8/2010 | Saadat |
| 2010/0228247 A1 | 9/2010 | Paul et al. |
| 2010/0241117 A1 | 9/2010 | Paul et al. |
| 2010/0312094 A1 | 12/2010 | Guttman et al. |
| 2010/0312096 A1 | 12/2010 | Guttman et al. |
| 2010/0331838 A1 | 12/2010 | Ibrahim et al. |
| 2011/0019893 A1 | 1/2011 | Rahn et al. |
| 2011/0029058 A1 | 2/2011 | Swanson |
| 2011/0042580 A1 | 2/2011 | Wilson et al. |
| 2011/0066147 A1 | 3/2011 | He et al. |
| 2011/0082450 A1 | 4/2011 | Melsky et al. |
| 2011/0082451 A1 | 4/2011 | Melsky et al. |
| 2011/0082452 A1 | 4/2011 | Melsky et al. |
| 2011/0117025 A1 | 5/2011 | Dacosta et al. |
| 2011/0144524 A1 | 6/2011 | Fish et al. |
| 2011/0224494 A1 | 9/2011 | Piskun et al. |
| 2011/0230903 A1 | 9/2011 | Bertolero |
| 2011/0275932 A1 | 11/2011 | Leblond et al. |
| 2011/0276046 A1 | 11/2011 | Heimbecher et al. |
| 2011/0282250 A1 | 11/2011 | Fung et al. |
| 2011/0313417 A1 | 12/2011 | De La Rama et al. |
| 2012/0029504 A1 | 2/2012 | Afonso et al. |
| 2012/0123276 A1 | 5/2012 | Govan et al. |
| 2012/0143177 A1 | 6/2012 | Avitall |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0197243 A1 | 8/2012 | Sherman et al. |
| 2012/0215112 A1 | 8/2012 | Lewis et al. |
| 2012/0220999 A1 | 8/2012 | Long |
| 2012/0259263 A1 | 10/2012 | Celermajer et al. |
| 2012/0323237 A1 | 12/2012 | Paul et al. |
| 2012/0326055 A1 | 12/2012 | Wilson et al. |
| 2013/0006116 A1 | 1/2013 | Kim et al. |
| 2013/0030425 A1 | 1/2013 | Stewart et al. |
| 2013/0079645 A1 | 3/2013 | Amirana et al. |
| 2013/0085416 A1 | 4/2013 | Mest |
| 2013/0096593 A1 | 4/2013 | Thapliyal et al. |
| 2013/0096594 A1 | 4/2013 | Thapliyal et al. |
| 2013/0102862 A1 | 4/2013 | Amirana et al. |
| 2013/0107002 A1 | 5/2013 | Kikuchi |
| 2013/0137949 A1 | 5/2013 | Freeman et al. |
| 2013/0150693 A1 | 6/2013 | D'Angelo et al. |
| 2013/0150732 A1 | 6/2013 | Manzke et al. |
| 2013/0158545 A1 | 6/2013 | Govan et al. |
| 2013/0172742 A1 | 7/2013 | Rankin et al. |
| 2013/0172875 A1 | 7/2013 | Govan et al. |
| 2013/0226163 A1 | 8/2013 | Peled et al. |
| 2013/0237841 A1 | 9/2013 | Freeman et al. |
| 2013/0253330 A1 | 9/2013 | Demos |
| 2013/0261455 A1 | 10/2013 | Thapliyal et al. |
| 2013/0267875 A1 | 10/2013 | Thapliyal et al. |
| 2013/0281920 A1 | 10/2013 | Hawkins et al. |
| 2013/0282005 A1 | 10/2013 | Koch et al. |
| 2013/0289358 A1 | 10/2013 | Melsky et al. |
| 2013/0296840 A1 | 11/2013 | Condie et al. |
| 2013/0310680 A1 | 11/2013 | Werahera et al. |
| 2013/0331831 A1 | 12/2013 | Werneth et al. |
| 2014/0031802 A1 | 1/2014 | Melsky |
| 2014/0058244 A1 | 2/2014 | Krocak |
| 2014/0058246 A1 | 2/2014 | Boveja et al. |
| 2014/0081253 A1 | 3/2014 | Kumar et al. |
| 2014/0088418 A1 | 3/2014 | Radulescu et al. |
| 2014/0107430 A1 | 4/2014 | Deno et al. |
| 2014/0121537 A1 | 5/2014 | Aeby et al. |
| 2014/0121660 A1 | 5/2014 | Hauck |
| 2014/0148703 A1 | 5/2014 | Deladi et al. |
| 2014/0163360 A1 | 6/2014 | Stevens-Wright et al. |
| 2014/0163543 A1 | 6/2014 | Allison et al. |
| 2014/0171806 A1 | 6/2014 | Govari et al. |
| 2014/0171936 A1 | 6/2014 | Govari et al. |
| 2014/0180273 A1 | 6/2014 | Nair |
| 2014/0194867 A1 | 7/2014 | Fish et al. |
| 2014/0194869 A1 | 7/2014 | Leo et al. |
| 2014/0275972 A1 | 9/2014 | George et al. |
| 2014/0276687 A1 | 9/2014 | Goodman et al. |
| 2014/0276771 A1 | 9/2014 | Miller et al. |
| 2014/0316280 A1 | 10/2014 | Mueller et al. |
| 2014/0324085 A1 | 10/2014 | Thapliyal et al. |
| 2014/0350547 A1 | 11/2014 | Sharareh et al. |
| 2014/0357956 A1 | 12/2014 | Salahieh et al. |
| 2015/0038824 A1 | 2/2015 | Lupotti |
| 2015/0073245 A1 | 3/2015 | Klimovitch et al. |
| 2015/0099979 A1 | 4/2015 | Caves et al. |
| 2015/0141847 A1 | 5/2015 | Sarvazyan |
| 2015/0164332 A1 | 6/2015 | Mercader et al. |
| 2015/0196202 A1 | 7/2015 | Mercader et al. |
| 2015/0327753 A1 | 11/2015 | Amirana et al. |
| 2015/0346100 A1 | 12/2015 | Racowsky et al. |
| 2016/0051321 A1 | 2/2016 | Salahieh et al. |
| 2016/0120599 A1 | 5/2016 | Amirana et al. |
| 2016/0120602 A1 | 5/2016 | Ransbury et al. |
| 2016/0143522 A1 | 5/2016 | Ransbury et al. |
| 2017/0135559 A1 | 5/2017 | Horrisberger et al. |
| 2018/0263476 A1 | 9/2018 | Amirana et al. |
| 2019/0053849 A1 | 2/2019 | Ransbury et al. |
| 2020/0008681 A1 | 1/2020 | Sarvazyan |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 106028914 | 10/2016 |
| DE | 102005021205 | 11/2006 |
| DE | 102011083522 | 3/2013 |
| EP | 2691041 | 2/2014 |
| EP | 2889013 A1 | 7/2015 |
| JP | 60182928 A | 9/1985 |
| JP | 63-262613 | 10/1988 |
| JP | 10150177 A | 6/1998 |
| JP | 2006158546 A | 6/2006 |
| JP | 2011212423 A | 10/2011 |

(56) References Cited

FOREIGN PATENT DOCUMENTS

| NL | 2002010 | 10/2009 |
|---|---|---|
| WO | WO 1997/037622 | 10/1997 |
| WO | 1999013934 A1 | 3/1999 |
| WO | 2001001854 | 1/2001 |
| WO | 2001072214 | 10/2001 |
| WO | 2003092520 A1 | 11/2003 |
| WO | 2004028353 A2 | 4/2004 |
| WO | 2006028824 | 3/2006 |
| WO | 2007109554 | 9/2007 |
| WO | 2007127228 A2 | 11/2007 |
| WO | 2008/028149 A2 | 3/2008 |
| WO | 2008114748 | 9/2008 |
| WO | 2008154578 | 12/2008 |
| WO | 2010075450 | 7/2010 |
| WO | 2011025640 | 3/2011 |
| WO | 2011113162 | 9/2011 |
| WO | 2012049621 A1 | 4/2012 |
| WO | 2012067682 A1 | 5/2012 |
| WO | 2013/044182 A1 | 3/2013 |
| WO | 2013068885 A1 | 5/2013 |
| WO | 2013116316 | 8/2013 |
| WO | 2013116316 A1 | 8/2013 |
| WO | 2013169340 A1 | 11/2013 |
| WO | 2014028770 | 2/2014 |
| WO | 2015/077474 A1 | 5/2015 |
| WO | 2015073871 | 5/2015 |
| WO | 2016/073476 | 5/2016 |
| WO | 2016073492 A1 | 5/2016 |
| WO | WO 2016/086160 | 6/2016 |
| WO | 2017/015257 A1 | 1/2017 |

OTHER PUBLICATIONS

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).
Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).
Office Action in U.S. Appl. No. 14/952,048 dated Aug. 27, 2018.
Office Action in U.S. Appl. No. 14/931,262 dated Aug. 28, 2018.
Office Action in U.S. Appl. No. 14/541,991 dated Sep. 13, 2018.
Office Action in U.S. Appl. No. 15/986,970 dated Sep. 17, 2018.
Office Action in U.S. Appl. No. 14/541,991 dated Feb. 28, 2017.
Office Action in U.S. Appl. No. 14/689,475 dated Apr. 13, 2017.
Office Action in U.S. Appl. No. 14/541,991 dated Jul. 13, 2017.
Office Action in U.S. Appl. No. 14/931,262 dated Apr. 20, 2018.
Office Action in U.S. Appl. No. 14/622,477 dated Jun. 5, 2018.
Office Action in U.S. Appl. No. 14/549,057 dated Jun. 15, 2018.
European Search Report completed Jun. 8, 2018 for EP 15 86 3645.
Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.
Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.

Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Smith, S., et al., "Imaging Appearances Following Thermal Ablation", Clinical Radiology, vol. 63, Issue 1, pp. 1-11, Jan. 2008.
Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swift, L.M., et al., "Properties of Blebbistatin for Cardiac Optical Mapping and Other Imaging Applications", European Journal of Physiology, vol. 464, Issue 5, pp. 503-512, Nov. 2012.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
European Search Report completed May 26, 2015 for EP 12 83 4435.
International Search Report dated Jan. 19, 2016 for PCT/US2015/058824.
Office Action in U.S. Appl. No. 14/689,475 dated Aug. 23, 2017.
Office Action in U.S. Appl. No. 14/622,477 dated Oct. 5, 2017.
Swift, Luther Mitchell, "Real-Time Visualization of Cardiac Ablation Lesions Using Endogenous NADH Fluorescence and Reflected Light", A dissertation submitted to the Faculty of the Columbian College of Arts and Sciences of The George Washington University in partial fulfillment of the requirements for the degree of Doctor of Philosophy, Jul. 23, 2013.
Office Action in U.S. Appl. No. 14/931,325 dated Mar. 22, 2018.
Anderson et al. "Real-time spectroscopic assessment of thermal damage: implications for radiofrequency ablation". J Gastrointest Surg. 2004; 8: 660-669.
Asfour et al, "Signal decomposition of transmembrane voltage-sensitive dye fluorescence using a multiresolution wavelet analysis" IEEE Trans Biomed Eng. 2011; 58: 2083-2093.
Boersma et al,."Pulmonary vein isolation by duty-cycled bipolar and unipolar radiofrequency energy with a multielectrode ablation catheter". Heart Rhythm5:1635-1642, 2008.
Buch et al. "Epicardial catheter ablation of atrial fibrillation." Minerva Med. 2009; 100: 151-157.
Cancio et al., "Hyperspectral Imaging: A New Approach to the Diagnosis of Hemorrhagic Shock", The Journal of Trauma, 2006, vol. 60, No. 5: 1087-1095.
Chance et al, "Fluorescence measurements of mitochondrial pyridine nucleotide in aerobiosis and anaerobiosis" Nature. 1959; 184: 931-4.
Coremans et al, "Pretransplantation assessment of renal viability with NADH fluorimetry", Kidney International, vol. 57, (2000), pp. 671-683.
D'Avila A. "Epicardial catheter ablation of ventricular tachycardia." Heart Rhythm. 2008; 5: S73-5.
Demos et al, "Real time assessment of RF cardiac tissue ablation with optical spectroscopy", Opt Express. 2008; 16: 15286-15296.
Dickfeld et al, "Characterization of Radiofrequency Ablation Lesions With Gadolinium-Enhanced Cardiovascular Magnetic Resonance Imaging" J Am Coll Cardiol. 2006; 47: 370-378.
Dukkipati et al, "Visual balloon-guided point-by-point ablation: reliable, reproducible, and persistent pulmonary vein isolation", Circ Arrhythm Electrophysiol. 2010; 3: 266-273.
Dumas et al, "Myocardial electrical impedance as a predictor of the quality of RF-induced linear lesions." Physiol Meas. 2008; 29: 1195-1207.
Fleming et al, "Real-time monitoring of cardiac redio-frequency ablation lesion formation using an optical coherence tomography forward-imaging catheter", Journal of Biomedical Optics, May/Jun. 2010, vol. 15(3).
Fleming et al, "Toward guidance of epicardial cardiac radiofrequency ablation therapy using optical coherence bmography" J Biomed Opt. 2010; 15: 041510.
Girard et al, "Contrast-enhanced C-arm CT evaluation of radiofrequency ablation lesions in the left ventricle", JACC Cardiovasc Imaging. 2011; 4: 259-268.

(56) References Cited

OTHER PUBLICATIONS

Grimard et al, "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial brillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Roger et al, "American Heart Association Stastics Committee and Stroke Subcommittee. Heart disease and stroke statistics—2011 update; a report from American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Sosa et al, "Epicardial mapping and ablation techniques to control ventricular tachycardia". J Cardiovasc Electrophysiol. 2005; 16: 449-452.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Van Haesendonck C, Sinnaeve A, Willems R, Vandenbulcke F, Stroobandt R, ."Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
Office Action in U.S. Appl. No. 13/624,899 dated Oct. 2, 2014.
Office Action in U.S. Appl. No. 13/624,902 dated Oct. 2, 2014.
Office Action in U.S. Appl. No. 14/549,057 dated Dec. 13, 2018.
Office Action in U.S. Appl. No. 14/622,477 dated Dec. 19, 2018.
Office Action in U.S. Appl. No. 15/986,970 dated Jan. 10, 2019.
Office Action in U.S. Appl. No. 14/931,262 dated Jan. 11, 2019.
Office Action in U.S. Appl. No. 16/167,933 dated Jan. 11, 2019.
Office Action in U.S. Appl. No. 14/541,991 dated Jan. 24, 2019.
Office Action in U.S. Appl. No. 14/952,048 dated Mar. 1, 2019.
Office Action in U.S. Appl. No. 14/931,262 dated Aug. 22, 2019.
Office Action in U.S. Appl. No. 14/622,477 dated Sep. 5, 2019.
Office Action in U.S. Appl. No. 15/986,970 dated Sep. 16, 2019.
Office Action in U.S. Appl. No. 16/167,933 dated Sep. 25, 2019.
Extended European Search Report dated Feb. 20, 2019 for EP 16 828 397.6.
Office Action in U.S. Appl. No. 14/952,048 dated Oct. 30, 2019.
Office Action in U.S. Appl. No. 14/541,991 dated Mar. 19, 2020.

SYSTEMS AND METHODS FOR LESION FORMATION AND ASSESSMENT

RELATED APPLICATIONS

This application claims the benefit of and priority to U.S. Provisional Application Ser. No. 62/194,276, filed on Jul. 19, 2015, which is incorporated herein by reference in its entirety.

FIELD

The present disclosure generally relates to catheters, and more particularly ablation and visualization catheters.

BACKGROUND

Atrial fibrillation (AF) is the most common sustained arrhythmia in the world, which currently affects millions of people. In the United States, AF is projected to affect 10 million people by the year 2050. AF is associated with increased mortality, morbidity, and an impaired quality of life, and is an independent risk factor for stroke. The substantial lifetime risk of developing AF underscores the public heath burden of the disease, which in the U.S. alone amounts to an annual treatment cost exceeding $7 billion.

Most episodes in patients with AF are known to be triggered by focal electrical activity originating from within muscle sleeves that extend into the Pulmonary Veins (PV). Atrial fibrillation may also be triggered by focal activity within the superior vena cava or other atrial structures, i.e. other cardiac tissue within the heart's conduction system. These focal triggers can also cause atrial tachycardia that is driven by reentrant electrical activity (or rotors), which may then fragment into a multitude of electrical wavelets that are characteristic of atrial fibrillation. Furthermore, prolonged AF can cause functional alterations in cardiac cell membranes and these changes further perpetuate atrial fibrillation.

Radiofrequency ablation (RFA), laser ablation and cryo ablation are the most common technologies of catheter-based mapping and ablation systems used by physicians to treat atrial fibrillation. Physicians use a catheter to direct energy to either destroy focal triggers or to form electrical isolation lines isolating the triggers from the heart's remaining conduction system. The latter technique is commonly used in what is called pulmonary vein isolation (PVI). However, the success rate of the AF ablation procedure has remained relatively stagnant with estimates of recurrence to be as high as 30% to 50% one-year post procedure. The most common reason for recurrence after catheter ablation is one or more gaps in the PVI lines. The gaps are usually the result of ineffective or incomplete lesions that may temporarily block electrical signals during the procedure but heal over time and facilitate the recurrence of atrial fibrillation.

Therefore, there is a need for system and method for forming and verifying proper lesions to improve outcomes and reduce costs.

SUMMARY

According to some aspects of the present disclosure, there is provided a catheter for visualizing ablated tissue comprising: a catheter body; a distal tip positioned at a distal end of the catheter body, the distal tip defining a illumination cavity, the distal tip having one or more openings for exchange of light energy between the illumination cavity and tissue; a light directing member disposed within the illumination cavity, the light directing member being configured to direct the light energy to and from the tissue through the one or more openings in the distal tip.

In some embodiments, the distal tip of the catheter may be configured to deliver ablation energy to the tissue, the ablation energy being selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

In some embodiments, the light directing member and the one or more openings are configured to enable illumination of tissue in a radial direction and an axial direction with respect to a longitudinal axis of the catheter. In some embodiments, the one or more openings are disposed along side walls of the distal tip and the light directing member is shaped to split light energy and specifically direct the light energy at an angle relative to the longitudinal axis of the catheter through the one or more openings. In some embodiments, the light directing member comprises one or more through-holes and the distal tip comprises one or more openings disposed on a front wall of the distal tip to enable passage of light in longitudinal direction through the light directing member and the one or more openings of the front wall. In some embodiments, the catheter may further comprise an ultrasound transducer.

According to some aspects of the present disclosure, there is provided a system for visualizing ablated tissue comprising a catheter comprising a catheter body; a distal tip positioned at a distal end of the catheter body, the distal tip defining a illumination cavity, the distal tip having one or more openings for exchange of light energy between the illumination cavity and tissue; a light directing member disposed within the illumination cavity, the light directing member being configured to direct the light energy to and from the tissue through the one or more openings in the distal tip; a light source; a light measuring instrument; and one or more optical fibers in communication with the light source and the light measuring instrument and extending through the catheter body into the illumination cavity of the distal tip, wherein the one or more optical fibers are configured to pass light energy from the light source to the light directing member for illuminating tissue outside the distal tip and the one or more optical fibers are configured to relay light energy reflected from the tissue to the light measuring instrument.

According to some aspects of the present disclosure, there is provided a method for visualizing ablated tissue comprising: advancing a catheter to a cardiac tissue in need of ablation, the catheter comprising a catheter body; a distal tip positioned at a distal end of the catheter body, the distal tip defining a illumination cavity, the distal tip having one or more openings for exchange of light between the illumination cavity and tissue; a light directing member disposed within the illumination cavity, the light directing member being configured to direct the light to and from the tissue through the one or more openings in the distal tip; causing the light directing member to direct light through the one or more openings in the distal tip of the catheter to excite nicotinamide adenine dinucleotide hydrogen (NADH) in an area of the cardiac tissue including ablated cardiac tissue and non-ablated cardiac tissue; collecting light reflected from the cardiac tissue through the one or more openings and directing the collected light to a light measuring instrument; imaging the area of the cardiac tissue to detect NADH fluorescence of the area of the cardiac tissue; and producing a display of the imaged, illuminated cardiac tissue, the display illustrating the ablated cardiac tissue as having less fluorescence than non-ablated cardiac tissue.

In some embodiments, the method may further include ablating tissue with the distal tip prior to imaging the tissue, and ablating additional non-ablated cardiac tissue identified by distinguishing between the ablated cardiac tissue and the non-ablated cardiac tissue based on the amount of fluorescence.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure generally relates to systems and methods for applying radiofrequency, laser or cryo ablation energy to the body to form therapeutic lesions. In some embodiments, the systems and methods of the present disclosure may be employed for imaging tissue using nicotinamide adenine dinucleotide hydrogen (NADH) fluorescence (fNADH). By way of a non-limiting example, the present systems and methods may be used during the treatment of Atrial Fibrillation (AF).

In general, the system may include a catheter with an optical system for exchanging light between tissue and the catheter. In some embodiments, the instant systems allow for direct visualization of the tissue's NADH fluorescence, or lack thereof, induced by ultraviolet (UV) excitation. The fluorescence signature returned from the tissue can be used to determine the presence or absence of ablation lesions in illuminated tissue as well as information about a lesion as it is forming during ablation. This optical tissue interrogation can be performed on various tissue types, including, without limitation, various cardiac tissues, endocardial tissue, epicardial tissue, myocardium tissue, valves, vascular structures, and fibrous and anatomical structures. The systems and methods of the present disclosure may be used to analyze tissue composition including, but not limited to, the presence of collagen and elastin. However, the presently disclosed methods and systems may also be applicable for analyzing lesions in other tissue types. The lesions to be analyzed may be created by application of ablation energy during the ablation procedure. In some embodiments, existing lesions, created by ablation or by other means, may also be analyzed using methods and systems disclosed herein.

Figure 1:
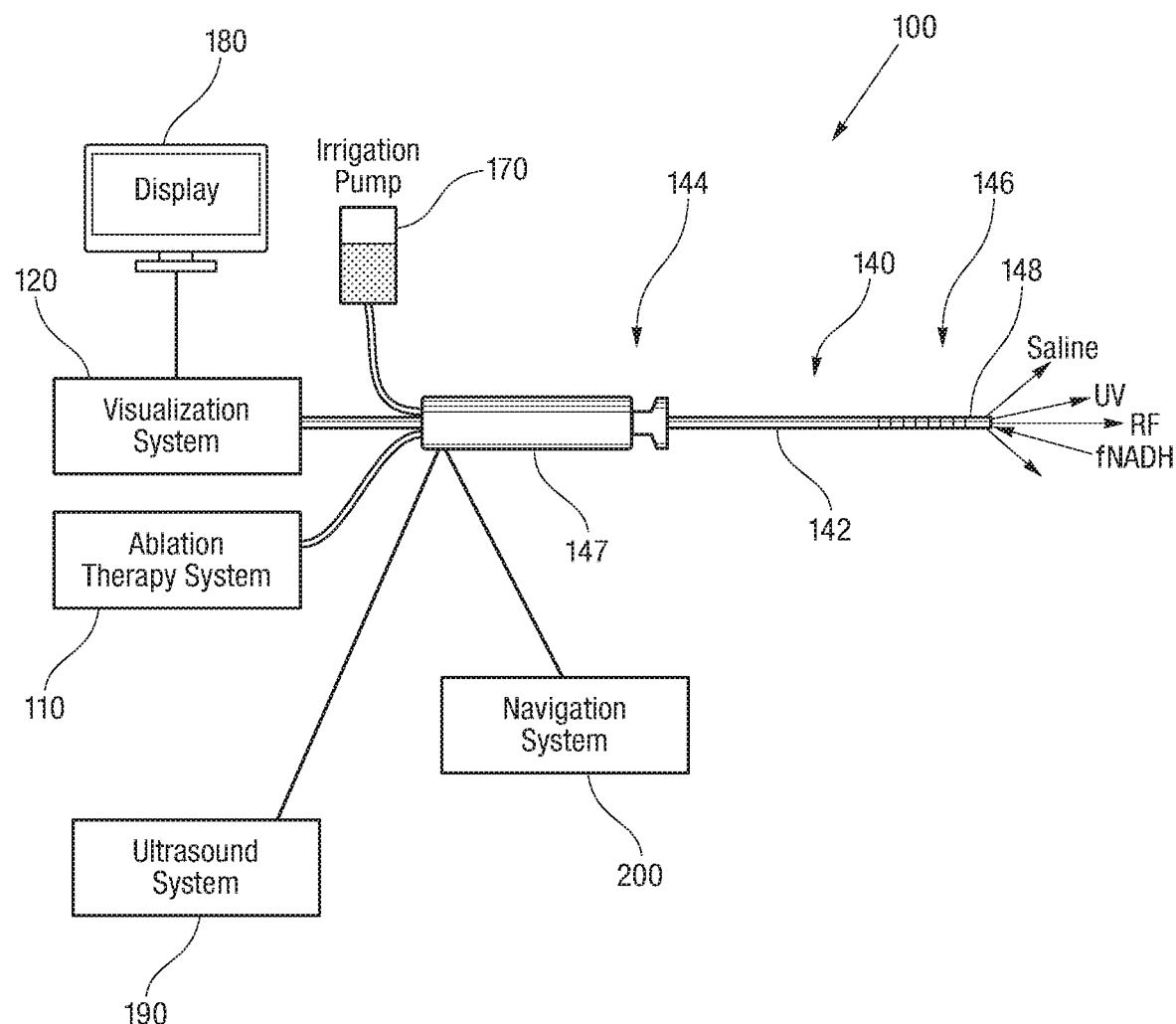
FIG. 1 is an embodiment of an ablation visualization system of the present disclosure.

In reference to FIG. 1, the system for providing ablation therapy 100 may include an ablation therapy system 110, a visualization system 120, and a catheter 140. In some embodiments, the system 100 may also include an irrigation system 170. The system may also include a display 180, which can be a separate display or a part of the visualization system 120, as described below.

In some embodiments, the ablation therapy system 110 is designed to supply ablation energy to the catheter 140. The ablation therapy system 110 may include one or more energy sources that can generate radiofrequency (RF) energy, microwave energy, electrical energy, electromagnetic energy, cryoenergy, laser energy, ultrasound energy, acoustic energy, chemical energy, thermal energy or any other type of energy that can be used to ablate tissue. In some embodiments, the system includes an RF generator, an irrigation pump 170, an irrigated-tip ablation catheter 140, and the visualization system 120.

Figure 2:
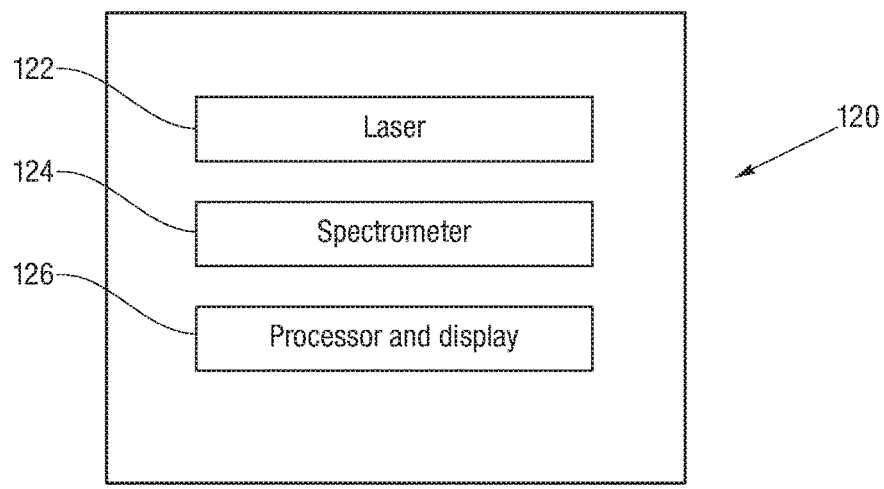
FIG. 2 is a diagram of a visualization system for use in connection with an ablation visualization system of the present disclosure.

In reference to FIG. 2, the visualization system 120 may include a light source 122, a light measuring instrument 124, and a computer system 126.

In some embodiments, the light source 122 may have an output wavelength within the target fluorophore (NADH, in some embodiments) absorption range in order to induce fluorescence in healthy myocardial cells. In some embodiments, the light source 122 is a solid-state laser that can generate UV light to excite NADH fluorescence. In some embodiments, the wavelength may be about 355 nm or 355 nm+/−30 nm. In some embodiments, the light source 122 can be a UV laser. Laser-generated UV light may provide much more power for illumination and may be more efficiently coupled into a fiber-based illumination system, as is used in some embodiments of the catheter. In some embodiments, the instant system can use a laser with adjustable power up to 150 mW.

The wavelength range on the light source 122 may be bounded by the anatomy of interest, a user specifically choosing a wavelength that causes maximum NADH fluorescence without exciting excessive fluorescence of collagen, which exhibits an absorption peak at only slightly shorter wavelengths. In some embodiments, the light source 122 has a wavelength from 300 nm to 400 nm. In some embodiments, the light source 122 has a wavelength from 330 nm to 370 nm. In some embodiments, the light source 122 has a wavelength from 330 nm to 355 nm. In some embodiments, a narrow-band 355 nm source may be used. The output power of the light source 122 may be high enough to produce a recoverable tissue fluorescence signature, yet not so high as to induce cellular damage. The light source 122 may be coupled to an optical fiber to deliver light to the catheter 140, as will be described below.

In some embodiments, the systems of the present disclosure may utilize a spectrometer as the light measuring instrument 124. In some embodiments, the light measuring instrument 124 may comprise a camera connected to the computer system 126 for analysis and viewing of tissue fluorescence. In some embodiments, the camera may have high quantum efficiency for wavelengths corresponding to NADH fluorescence. One such camera is an Andor iXon DV860. The spectrometer 124 may be coupled to an imaging bundle that can be extended into the catheter 140 for visualization of tissue. In some embodiments, the imaging bundle for spectroscopy and the optical fiber for illumination may be combined. An optical bandpass filter of between 435 nm and 485 nm, in some embodiments, of 460 nm, may be inserted between the imaging bundle and the camera to block light outside of the NADH fluorescence emission band. In some embodiments, other optical bandpass filters may be inserted between the imaging bundle and the camera to block light outside of the NADH fluorescence emission band selected according to the peak fluorescence of the tissue being imaged.

In some embodiments, the light measuring instrument 124 may be a CCD (charge-coupled device) camera. In some embodiments, the spectrometer 124 may be selected so it is capable of collecting as many photons as possible and that contributes minimal noise to the image. Usually for fluorescence imaging of live cells, CCD cameras should have a quantum efficiency at about 460 nm of at least between 50-70%, indicating that 30-50% of photons will be disregarded. In some embodiments, the camera has quantum efficiency at 460 nm of about 90%. The camera may have a sample rate of 80 KHz. In some embodiments, the spectrometer 124 may have a readout noise of 8 e– (electrons) or less. In some embodiments, the spectrometer 124 has a minimum readout noise of 3e–. Other light measuring instruments may be used in the systems and methods of the present disclosure.

The optical fiber 150 can deliver the gathered light to a long pass filter that blocks the reflected excitation wavelength of 355 nm, but passes the fluoresced light that is emitted from the tissue at wavelengths above the cutoff of the filter. The filtered light from the tissue can then be captured and analyzed by a high-sensitivity spectrometer 124. The computer system 126 acquires the information from the spectrometer 124 and displays it to the physician. The computer 126 can also provide several additional functions including control over the light source 122, control over the spectrometer 124, and execution of application specific software.

In some embodiments, the digital image that is produced by analyzing the light data may be used to do the 2D and 3D reconstruction of the lesion, showing size, shape and any other characteristics necessary for analysis. In some embodiments, the image bundle may be connected to the spectrometer 124, which may generate a digital image of the lesion being examined from NADH fluorescence (fNADH), which can be displayed on the display 180. In some embodiment, these images can be displayed to the user in real time. The images can be analyzed by using software to obtain real-time details (e.g. intensity or radiated energy in a specific site of the image) to help the user to determine whether further intervention is necessary or desirable. In some embodiments, the NADH fluorescence may be conveyed directly to the computer system 126.

In some embodiments, the optical data acquired by the light measuring instrument can be analyzed to provide information about lesions during and after ablation including, but not limited to lesion depth and lesion size. In some embodiments, data from the light measuring instrument can be analyzed to determine if the catheter 140 is in contact with the myocardial surface and how much pressure is applied to the myocardial surface by the tip of the catheter. In some embodiments, data from the spectrometer 124 is analyzed to determine the presence of collagen or elastin in the tissue. In some embodiments, data from the light measuring instrument is analyzed and presented visually to the user via a graphical user interface in a way that provides the user with real-time feedback regarding lesion progression, lesion quality, myocardial contact, tissue collagen content, and tissue elastin content.

In some embodiments, the system 100 of the present disclosure may further include an ultrasound system 190. The catheter 140 may be equipped with ultrasound transducers in communication with the ultrasound system. In some embodiments, the ultrasound may show tissue depths, which in combination with the metabolic activity or the depth of lesion may be used to determine if definitively say if a lesion is in fact transmural or not.

Referring back to FIG. 1, the catheter 140 includes a catheter body 142 having a proximal end 144 and a distal end 146. The catheter body 142 may be made of a biocompatible material, and may be sufficiently flexible to enable steering and advancement of the catheter 140 to a site of ablation. In some embodiments, the catheter body 142 may have zones of variable stiffness. For example, the stiffness of the catheter 140 may increase from the proximal end 144 toward the distal end 146. In some embodiments, the stiffness of the catheter body 142 is selected to enable delivery of the catheter 140 to a desired cardiac location. In some embodiments, the catheter 140 can be a steerable, irrigated radiofrequency (RF) ablation catheter that can be delivered through a sheath to the endocardial space, and in the case of the heart's left side, via a standard transseptal procedure using common access tools. The catheter 140 may include a handle 147 at the proximal end 144. The handle 147 may be in communication with one or more lumens of the catheter to allow passage of instruments or materials through the catheter 140. In some embodiments, the handle 147 may include connections for the standard RF generator and irrigation system for therapy. In some embodiments, the catheter 140 may also include one more adaptors configured to accommodate the optical fiber 150 for illumination and spectroscopy.

Figure 3:
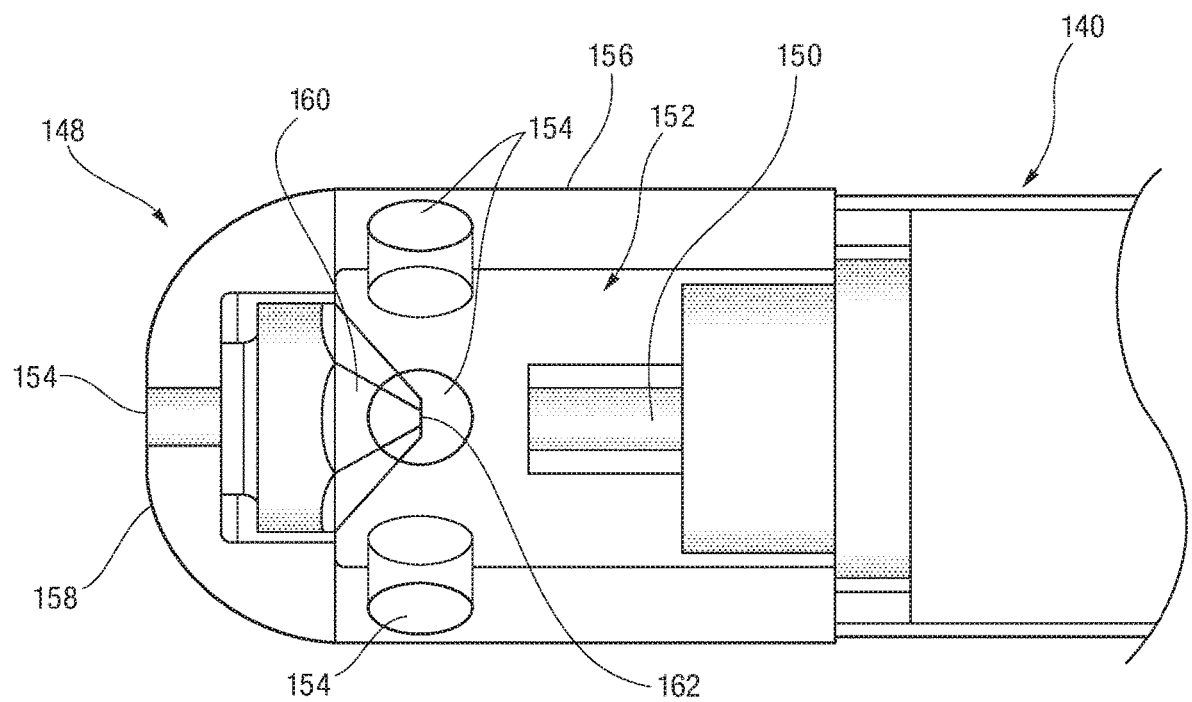
FIG. 3 illustrates an embodiment of a distal tip of a catheter of the present disclosure.

In reference to FIG. 3, at the distal end 146, the catheter 140 may include a distal tip 148, having a side wall 156 and a front wall 158. The front wall 158 may be, for example, flat, conical or dome shaped. In some embodiments, the distal tip 148 may be configured to act as an electrode for diagnostic purposes, such as electrogram sensing, for therapeutic purposes, such as for emitting ablation energy, or both. In some embodiments where ablation energy is required, the distal tip 148 of the catheter 140 could serve as an ablation electrode or ablation element.

In the embodiments where RF energy is implemented, the wiring to couple the distal tip 148 to the RF energy source (external to the catheter) can be passed through a lumen of the catheter. The distal tip 148 may include a port in communication with the one or more lumens of the catheter. The distal tip 148 can be made of any biocompatible material. In some embodiments, if the distal tip 148 is configured to act as an electrode, the distal tip 148 can be made of metal, including, but not limited to, platinum, platinum-iridium, stainless steel, titanium or similar materials.

In reference to FIG. 3, an optical fiber or an imaging bundle 150 may be passed from the visualization system 120, through the catheter body 142, and into an illumination cavity or compartment 152, defined by the distal tip 148. The distal tip 148 may be provided with one or more openings 154 for exchange of light energy between the illumination cavity 152 and tissue. In some embodiments, even with multiple openings 154, the function of the distal tip 148 as an ablation electrode is not compromised. This light is delivered by the fiber 150 to the distal tip 148, where it illuminates the tissue in the proximity of the distal tip 148. This illumination light is either reflected or causes the tissue to fluoresce. The light reflected by and fluoresced from the tissue may be gathered by the optical fiber 150 within the distal tip 148 and carried back to the visualization system 120. In some embodiments, the same optical fiber or bundle of fibers 150 may be used to direct light to the light directing member 160 to illuminate tissue outside the catheter 140 in one or more directions and to collect light from the tissue.

In some embodiments, the one or more openings 154 may be provided in the side wall 156 of the distal tip 148, the front wall 158, or both. In some embodiments, the one or more openings 154 may be disposed circumferentially along the distal tip 148 around the entire circumference of the distal tip 148. In some embodiments, the one or more openings 154 may be disposed equidistantly from one another. The number of the openings may be determined by the desired angle of viewing coverage. For example, with 3 openings equally spaced, illumination and returned light occur at 120-degree increments (360 degrees divided by 3). In some embodiments, the one or more openings 154 may be provided in multiple rows along the side walls 156 of the distal tip 148. In some embodiments, the distal tip 148 may include 3 or 4 openings in the side wall 156. In some embodiments, a single opening may be provided in the center of the front wall 158. In some embodiments, multiple openings 154 may be provided in the front wall 158. In some embodiments, the distal tip 148 is provided with 3 side openings and 1 front opening. The one or more openings 154 may also serve as an irrigation port in connection with the irrigation system. In some embodiments light is only directed through some of the side openings 154. For example, in some embodiments there may exist 6 openings in the side wall 156, but light may be directed through only 3 of the openings, while the other openings may be used for irrigation.

To enable the light energy exchange between the illumination cavity 152 and tissue over multiple paths (axially and radially with respect to the longitudinal central axis of the catheter), a light directing member 160 may be provided in the illumination cavity 152. The light directing member 160 may direct the illumination light to the tissue and direct the light returned through the one or more openings 154 within the distal tip 148 to the optical fiber 150. The light directing member 160 may also be made from any biocompatible material with a surface that reflects light or can be modified to reflect light, such as for example, stainless steel, platinum, platinum alloys, quartz, sapphire, fused silica, metallized plastic, or other similar materials. In some embodiments, the light directing member 160 may comprise a highly polished mirror. The light directing member 160 may be conical (i.e. smooth) or faceted with any number of sides. The light directing member 160 may be shaped to bend the light at any desired angle. In some embodiments, the light directing member 160 may be shaped to reflect the light only through the one or more openings. In some embodiments, the material for the light directing member 160 is chosen from materials that do not fluoresce when exposed to illumination between 310 nm to 370 nm.

In some embodiments, as shown in FIG. 3, the light directing member 160 may include one or more holes 162 through the centerline of the mirror, which allow illumination and reflected light to pass in both directions axially, directly in line with the catheter 140. Such an axial path may be useful when the distal-most surface of the distal tip 148 is in contact with the anatomy. The alternateradial paths may be useful when the anatomy will not allow the distal-most surface of the distal tip 148 to be in contact with the target site as is sometimes the case in the left atrium of the patient during pulmonary vein isolation procedures, common in treating atrial fibrillation. In some embodiments, in all pathways, lensing may not be required and the optical system is compatible with the irrigation system 170 as the light passes through the cooling fluid, which is often saline. The irrigation system 170 may also serve to flush the blood from the holes 162, thus keeping the optical components clean.

Figure 4A:
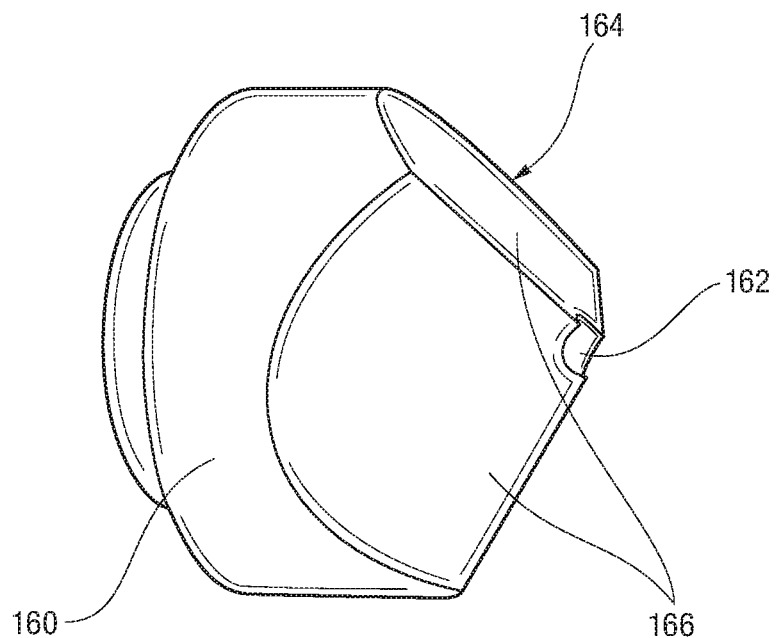
FIG. 4A and FIG. 4B illustrate an embodiment of a light directing member of a catheter of the present disclosure.
Figure 4B:
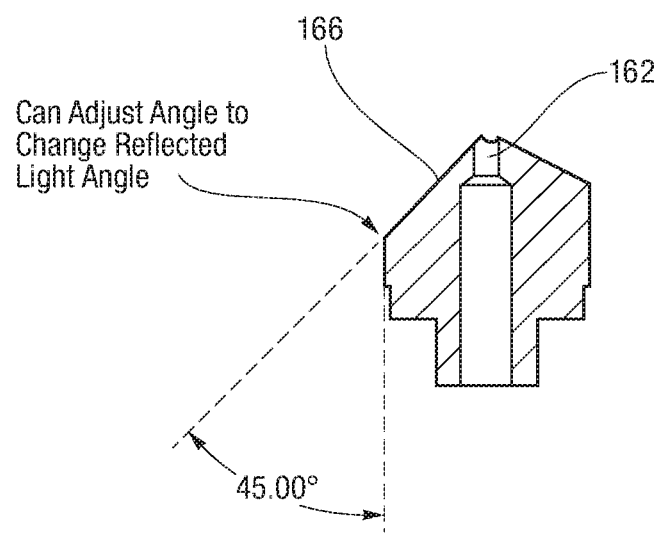

In reference to FIG. 4A, the light directing member 160 may have a front face 164 with multiple, angled facets 166. In some embodiments, the light directing member 160 may include 3 or 4 equidistant facets, although more or less facets may be used. In some embodiments, the number of facets 166 may correspond to the number of the openings 154 in the side wall 156. In some embodiments, there may be fewer facets 166 than the openings 154 in the side wall 156. In some embodiments, as shown in FIG. 4B, the facets 166 may be positioned at 45 degrees relative to central axis of the light directing member 160 (135 degrees relative to the axis of the catheter). In some embodiments, the facets 166 may be positioned at greater or lesser angles than 45 degrees in order to direct light more distally or more proximally.

Figure 5A:
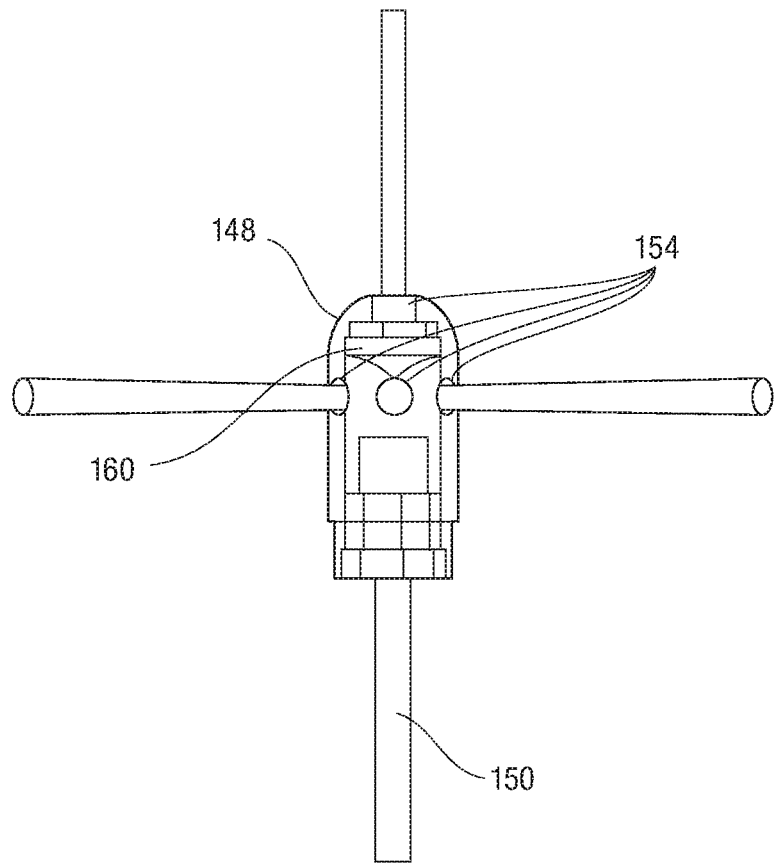
FIG. 5A and FIG. 5B illustrate an embodiment of a distal tip of a catheter of the present disclosure.

In reference to FIG. 5A, the light directed onto the light directing member 160 from the optical fiber 150 may be reflected by the light directing member 160. Some of the reflected light may exit the distal tip 148 through the one or more openings 154 in the side wall 156 of the distal tip 148. The light directing member may separate or split the light beam shined on the light directing member into multiple beams and specifically directing the split beams to exit through the corresponding openings 154. In this manner, the intensity of light from the light source may be substantially conserved and the intensity of illuminating the tissue may be increased. Otherwise, if the light is diffused through the illumination cavity, without the light directing member focusing the light into the openings 154, the intensity of the light illuminating the tissue may be insufficient for tissue imaging. In addition, in some embodiments, the light directing member is configured to collect light beams reflected from the tissue and to direct them the optical fiber, which can them relay them to the light measuring instrument. In some embodiments, the beams received from tissue may be combined before being sent to the optical fiber. In some embodiments, all light delivered into the illumination cavity may be directed by the light directing member to exit the illumination cavity 152 through the openings 154. In addition, light can also pass through the holes 162 in the light directing member 160 and through the openings 154 in the front wall 158 of the distal tip 148. By aligning the light directing member 160, the optical fiber 150 and the openings 154, the intensity of light to tissue may be adjusted and maximized. The angle of the facets 166, the size, number, and location of the openings 154, and the size, number, and location of holes in the light directing member 160 can be adjusted and optimized to provide the desired balance of light returned from tissue illuminated at the distal tip 148 of the catheter via the openings in light directing member 160 and the light returned from tissue illuminated via the openings 154.

Figure 5B:
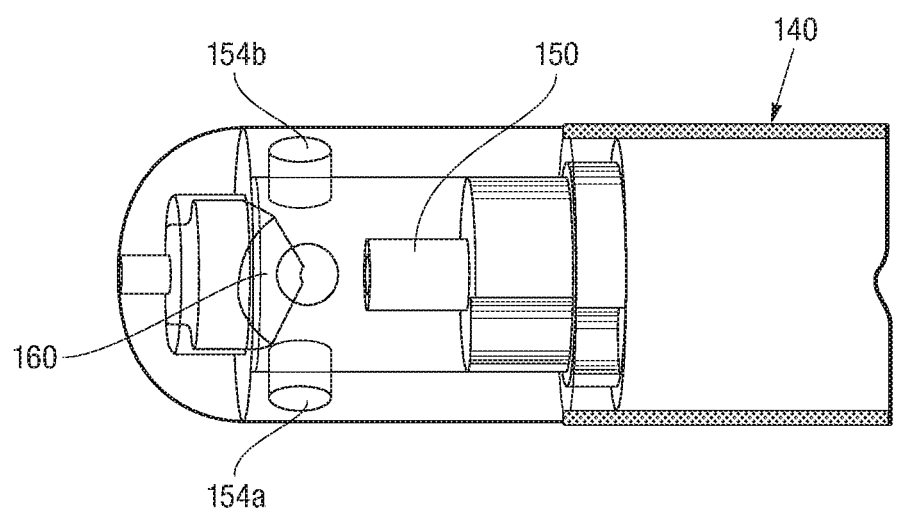

As shown in FIG. 5B, in some embodiments, the openings 154 may be directly in line with the facets 166 of the light directing member 160. In some embodiments, the correspondence between the openings 154 and the facets 166 may be different than 1:1. In some embodiments, the catheter 140 may include 3 openings or 4 openings corresponding to 3 facets or 4 facets 166, respectively, of the light directing member 160. It should be noted that, in some embodiments, some of the openings 154 may not be used for exchange of light due to the shape and orientation of the openings 154 and the light directing member 160, but are only used for irrigation purposes. As shown in FIG. 5B, the openings 154*a* may be aligned with the facets 166 for exchange of light, while openings 154*b* are not aligned with the facets 166, and thus are used primarily for irrigation, even if additional light is exchanged.

Figure 6A:
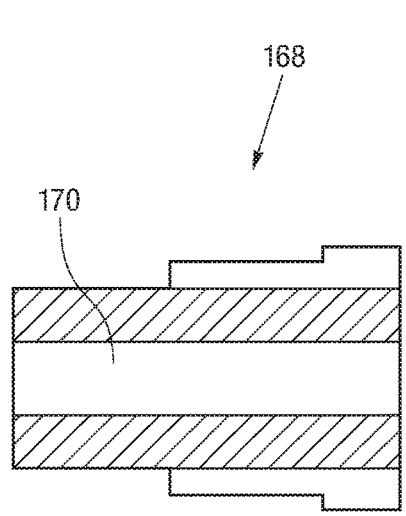
FIG. 6A, FIG. 6B, FIG. 6C and FIG. 6D illustrate an optical fiber aligner of a catheter of the present disclosure.
Figure 6B:
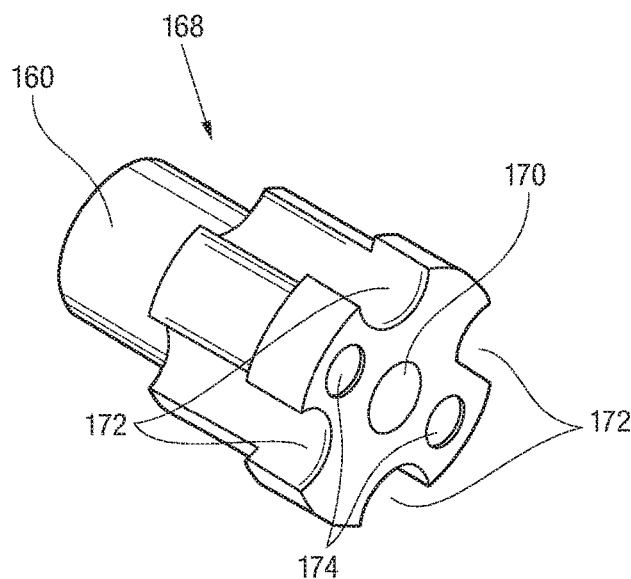

In reference to FIG. 6A and FIG. 6B, in some embodiments, a fiber aligner 168 may be provided in the distal tip 148 to align the optical fiber 150 with the light directing member 160. The fiber aligner 168 may include a fiber lumen 170 through which the optical fiber 150 may be advanced to align the optical fiber 150 with the light directing member 160. In some embodiments, the central axis of the optical fiber 150 may be aligned with the center axis of the light directing member 160 to uniformly illuminate the facets 166 of the light directing member 160 and to allow illumination in the central hole for illumination and return in the longitudinal direction. For example, the fiber lumen 170 may extend along the center axis of the fiber aligner 168 to center the optical fiber 150 relative to the light directing member 160. The position of the fiber in the fiber aligner 168 may be optimized to distribute light as desired between the central hole in the light directing member 160 and the openings 154 to maximize tissue fluorescence for the ablation application of interest.

Figure 6C:
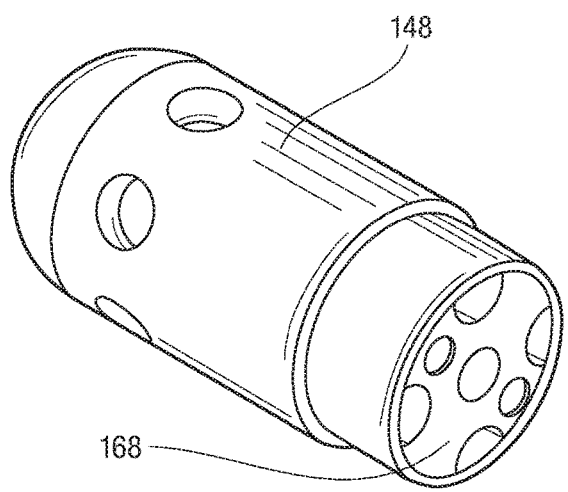
Figure 6D:
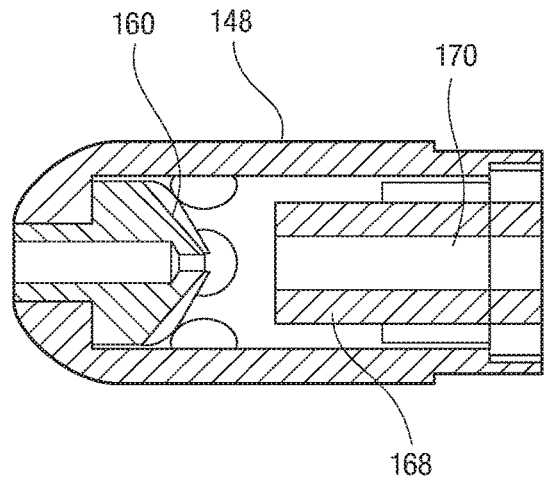

As shown in FIG. 6C and FIG. 6D, the fiber aligner 168 may be inserted into the distal tip 148. When the optical fiber 150 is advanced through the fiber lumen 170 of the fiber aligner 168, the optical fiber 150 will assume a desired orientation and position relative to the light directing member 160.

Referring back to FIG. 6B, in some embodiments, the fiber aligner 168 may include one or more cut outs 172 and one or more ports 174. In this manner, when the fiber aligner 168 is inserted into the distal end 144 of the catheter 140, the cut outs 172 and the ports 174 allow passage of instruments and materials (such as, for example, irrigation fluid and electrode wiring for ablation into the distal tip 148).

Figure 7A:
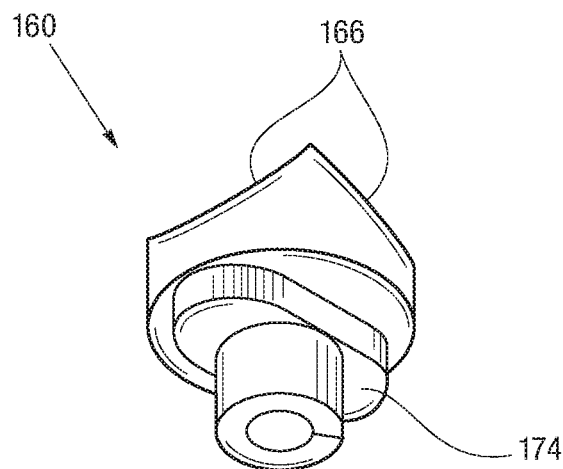
FIG. 7A and FIG. 7B illustrate an embodiment of a light directing member of the present disclosure.
Figure 7B:
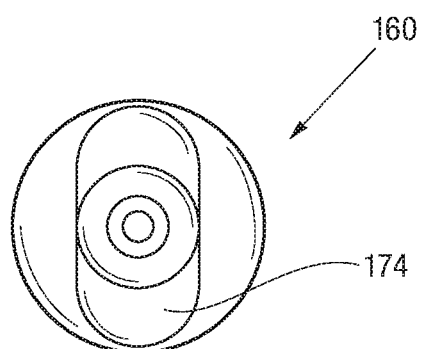

In reference to FIG. 7A and FIG. 7B, the light directing member 160 may be provided with a key member 174 to help align the facets 166 of the light directing member 160 with the one or more openings 154. The angle of the facets on the light directing member 160 may align with the openings 154 on the distal tip 148. If they are misaligned, the light path may become inefficient. To ensure this alignment, in some embodiments, the light directing member 160 and the distal tip 148 have symmetrical key features so that the alignment of the facets 166 and the openings are deterministic. Once in place, a variety of technologies can be used to secure the light directing member 160 to the distal tip 148.

Figure 8A:
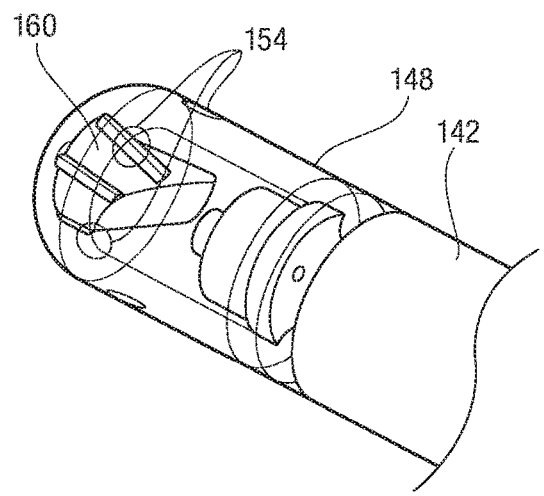
FIGS. 8A-8D illustrate various embodiments of a catheter of the present disclosure.
Figure 8B:
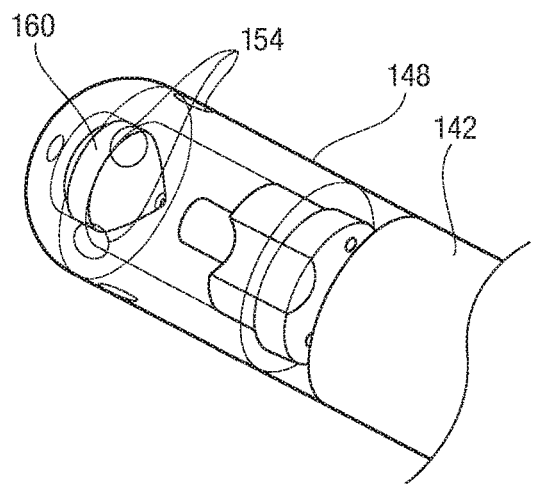
Figure 8C:
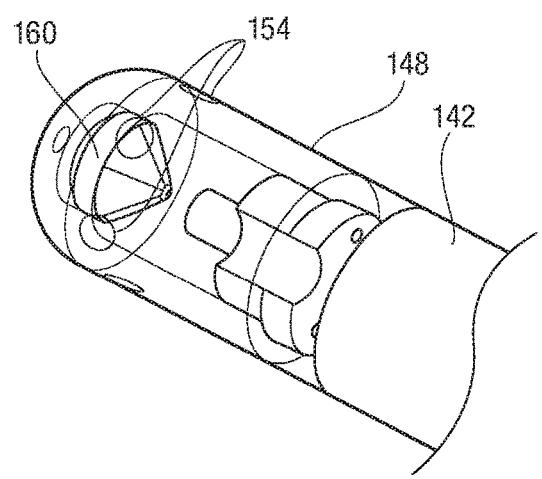
Figure 8D:
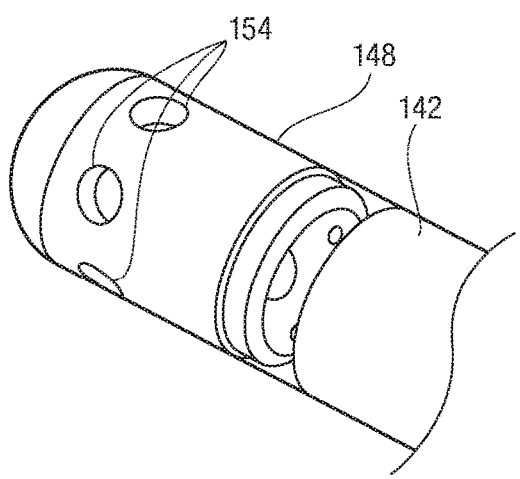

In reference to FIG. 8A and FIG. 8B, in some embodiments, the light directing member 160 may comprise a single faceted mirror that is capable of illuminating and receiving light in only one direction at a time. In some embodiments, such light directing member 160 may be rotatable relative to the catheter 140 to align the opening 154 in the side wall 156 with the target site. There are many ways of implementing a rotating mirror including, without limitation, a hydraulic turbine mechanism, having a torquing mechanism in the handle 147 of the catheter 140 coupled to the light directing mirror. In reference to FIG. 8B, in some embodiments, a stationary mirror may be provided with a conical as opposed to a faceted geometry. FIG. 8C and FIG. 8D illustrate another embodiment of the light directing member 160 with 6 facets.

Figure 9:
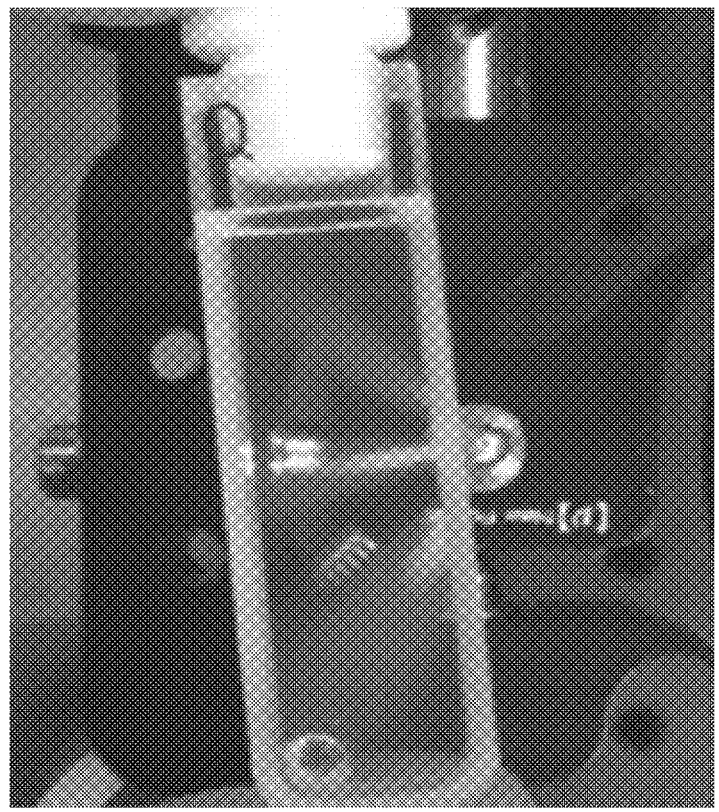
FIG. 9 illustrates an embodiment of a catheter of the present disclosure illuminating a fluorescent solution.

FIG. 9 illustrates a catheter 140 of the present disclosure oriented pointing at the viewer. When a vial of solution that fluoresces at the same wavelengths as NADH is held next to the catheter 140, light pathways that emanate radially from the distal tip 148 are interacting with the vial of solution. The pathways emanating from the opposite side of the distal tip 148 are not visible due to lack of fluorescence.

As noted above, the system 100 may also include an irrigation system 170. In some embodiments, the irrigation system 170 pumps saline into the catheter to cool the tip electrode during ablation therapy. This may help to prevent steam pops and char (i.e. clot that adheres to the tip that may eventually dislodge and cause a thrombolytic event) formation. For the proposed optical system, the fluid flow may clear the opening in the distal tip 148 of any blood that otherwise would otherwise absorb the illumination light.

The irrigation system 170 may be connected to the one or more openings in the distal tip 148 and can be used, for example, for flushing the openings with fluid to clear the tip of blood, cooling the tissue-electrode interface, prevention of thrombus formation, among many other possible uses. In some embodiments, the irrigation fluid is maintained at a positive pressure relative to pressure outside of the catheter for continuous flushing of the one or more openings 154.

Figure 10:
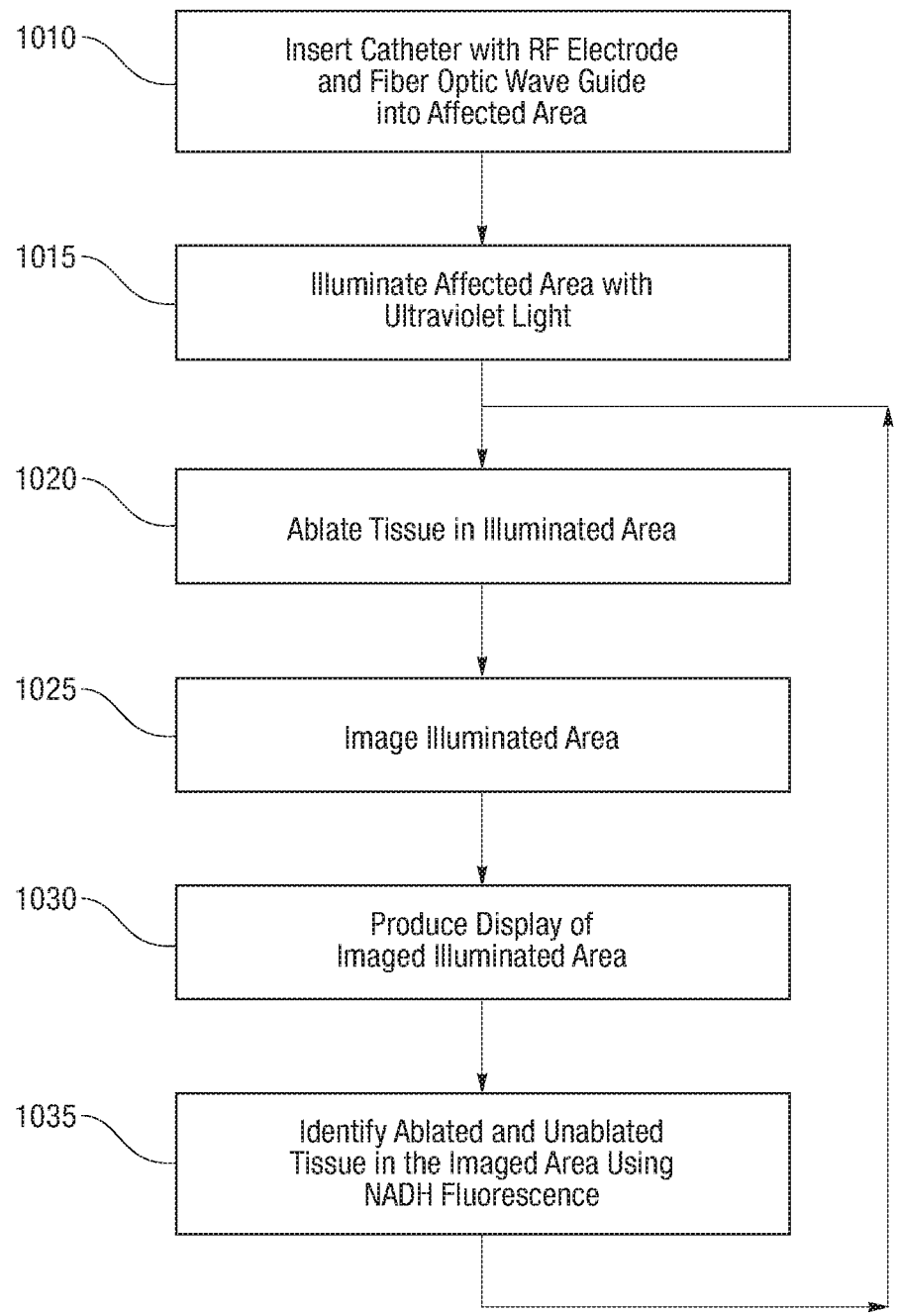
FIG. 10 is a flow chart of a method of using a system of the present disclosure.

In reference to FIG. 10, operation of the systems 100 of the present disclosure is illustrated. Initially, the catheter 140 is inserted into the area of heart tissue affected by the atrial fibrillation, such as the pulmonary vein/left atrial junction or another area of the heart (step 1010). Blood may be removed from the visual field, for example, by irrigation. The affected area may be illuminated by ultra-violet light reflected from the light directing member 160 (step 1015). Tissue in the illuminated area may be ablated (step 1020), either before, after, or during illumination. Either point-to-point RF ablation or cryoablation or laser or other known ablation procedures may be employed using the systems of the present disclosure.

Still referring to FIG. 10, the illuminated area may be imaged with the light directing member receiving the light from the tissue and directing such light to the optical fiber, which can then pass the light to the spectrometer (step 1025). In some embodiments, the methods of the present disclosure rely on imaging of the fluorescence emission of NADH, which is a reduced form of nicotinamide adenine dinucleotide (NAD+). NAD+ is a coenzyme that plays important roles in the aerobic metabolic redox reactions of all living cells. It acts as an oxidizing agent by accepting electrons from the citric acid cycle (tricarboxylic acid cycle), which occurs in the mitochondrion. By this process, NAD+ is thus reduced to NADH. NADH and NAD+ are most abundant in the respiratory unit of the cell, the mitochondria, but are also present in the cytoplasm. NADH is an electron and proton donor in mitochondria to regulate the metabolism of the cell and to participate in many biological processes including DNA repair and transcription.

By measuring the UV-induced fluorescence of tissue, it is possible to learn about the biochemical state of the tissue. NADH fluorescence has been studied for its use in monitoring cell metabolic activities and cell death. Several studies in vitro and in vivo investigated the potential of using NADH fluorescence intensity as an intrinsic biomarker of cell death (either apoptosis or necrosis) monitoring. Once NADH is released from the mitochondria of damaged cells or converted to its oxidized form (NAD+), its fluorescence markedly declines, thus making it very useful in the differentiation of a healthy tissue from a damaged tissue. NADH can accumulate in the cell during ischemic states when oxygen is not available, increasing the fluorescent intensity. However, NADH presence disappears all together in the case of a dead cell. The following table summarizes the different states of relative intensity due to NADH fluorescence:

| Cellular State | NADH Presence | Relative Changes of Autofluorescense intensity |
| --- | --- | --- |
| Metabolically Active | Normal | Baseline |
| Metabolically Active but Impaired (Ischemia) | Increased due to Hypoxia | Increased |
| Metabolically Inactive (Necrotic) | None | Full Attenuation |

Still referring to FIG. 10, while both NAD+ and NADH absorb UV light quite readily, NADH is autofluorescent in response to UV excitation whereas NAD+ is not. NADH has a UV excitation peak of about 340-360 nm and an emission peak of about 460 nm. In some embodiments, the methods of the present disclosure may employ excitation wavelengths between about 330 to about 370 nm. With the proper instrumentation, it is thus possible to image the emission wavelengths as a real-time measure of hypoxia as well as necrotic tissue within a region of interest. Furthermore, in some embodiments, a relative metric can be realized with a grayscale rendering proportionate to NADH fluorescence.

Under hypoxic conditions, the oxygen levels decline. The subsequent fNADH emission signal may increase in intensity indicating an excess of mitochondrial NADH. If hypoxia is left unchecked, full attenuation of the signal will ultimately occur as the affected cells along with their mitochondria die. High contrast in NADH levels may be used to identify the perimeter of terminally damaged ablated tissue.

To initiate fluorescence imaging, NADH may be excited by the UV light from the light source, such as a UV laser. NADH in the tissue specimen absorbs the excitation wavelengths of light and emits longer wavelengths of light. The emission light may be collected and passed back to the spectrometer, and a display of the imaged illuminated area may be produced on a display (step 1030), which is used to identify the ablated and unablated tissue in the imaged area based on the amount of NADH florescence (step 1035). For example, the sites of complete ablation may appear as completely dark area due to lack of fluorescence. Accordingly, the areas of ablation may appear markedly darker when compared to the surrounding unablated myocardium, which has a lighter appearance. This feature may enhance the ability to detect the ablated areas by providing marked contrast to the healthy tissue and even more contrast at the border zone between ablated and healthy tissue. This border area is the edematous and ischemic tissue in which NADH fluorescence becomes bright white upon imaging. The border zone creates a halo appearance around the ablated central tissue.

The process may then be repeated by returning to the ablation step, if necessary, to ablate additional tissue. It should be recognized that although FIG. 10 illustrates the steps being performed sequentially, many of the steps may be performed simultaneously or nearly simultaneously, or in a different order than shown in FIG. 10. For example, the ablation, imaging and display can occur at the same time, and the identification of the ablated and unablated tissue can occur while ablating the tissue.

In some embodiments, the system of the present disclosure comprises a catheter, a light source, and a light measuring instrument. In some embodiments, the system further comprises an optical detection system having an optical detection fiber, the optical detection system being independent or immune from electrical or RF energy noise. In some embodiments, the optical detection fiber does not conduct electrically and an RF energy does not produce electromagnetic energy in a range of interest to the system.

In some embodiments, the system is adapted to optically interrogate a catheter environment in a biologic system. In some embodiments, the system is adapted to optically interrogate in real-time, via an NADH fluorescence, the catheter environment to determine or assess one or more of a complete or a partial immersion of an electrode in a blood pool. For example, the optical system can detect, by inference, that the catheter tip is completely or partially immersed in the blood pool. The reason for this is because unlike the tissue or vasculature that return a positive optical signature, the blood completely absorbs the illumination light at this wavelength and thus returns a null optical signature. This feature of complete absorption provides optical isolation and therefore noise insulation. The instrument can use this situation for optical calibration and the elimination of stray optical signatures coming from the catheter itself. In addition, the system may be used for a qualitative and or a quantitative contact assessment between a catheter tip and a tissue, a qualitative and or a quantitative assessment of a catheter contact stability, an ablation lesion formation in real time, an ablation lesion progression monitoring, a determination of when to terminate a lesion, an identification of edematous zones which usually occur on a periphery of an ablation site and which can be associated with an incomplete ablation lesion, an ablation lesion depth, a cross-sectional area of the lesion, a temperature of the lesion, a recognition of steam formation or another physiologic parameter change to predict the onset of a steam pop, a formation of a char at a tip electrode during or after the ablation lesion formation, a detection of ischemia, a detection of a level of the ischemia, an ablation lesion assessment post lesion formation, an identification of edematous zones for re-ablation since edematous zones include myocardium that is electrically stunned, and a mapping of a location of previously ablated tissue by distinguishing metabolically active tissue from metabolically inactive tissue In some embodiments, the system is adapted to optically interrogate a tissue parameter of an NADH fluorescence (fNADH).

In some embodiments, the system is adapted to optically interrogate a tissue, wherein the system analyzes parameters including a metabolic state of the tissue as well as a tissue composition of the tissue.

In some embodiments, the system is adapted to illuminate a tissue with a wavelength wherein illuminating leads to several optical responses. In some embodiments the optical responses comprises a myocardium containing NADH fluorescing if it is in a healthy metabolic state. In some embodiments, other tissues, such as collagen or elastin, fluoresce at different wavelengths, and the system uses a measurement of this information to determine a composition (i.e. collagen or elastin) of the tissue in contact with the catheter. In some embodiments the composition comprises myocardium, muscle, and myocardial structures such as valves, vascular structures, and fibrous or anatomical components. In some embodiments the composition comprises collagen, elastin, and other fibrous or support structures.

In some embodiments, a catheter of the present disclosure comprises a catheter body, a tip electrode, and one or more sensing electrodes. In some embodiments the catheter further comprises one or more zones of different flexibility, the zones of flexibility being in combination with a deflection mechanism adapted to allow a distal portion of the catheter to be bent for ease of navigation for a physician. In some embodiments, the zones of flexibility are located at the distal portion of the catheter, while a main body of the catheter is kept relatively stiff for pushability. In some embodiments, the main body of the catheter body is flexible so that the physician can use a robotic system for catheter navigation. In some embodiments the catheter is flexible and capable of being manipulated within a catheter sheath manually or robotically.

In some embodiments, the catheter further comprises a deflection mechanism adapted to deflect the catheter tip for navigation. In some embodiments the deflection mechanism comprises one or more pull wires that are manipulated by a catheter handle and which deflect the distal portion of the catheter in one or more directions or curve lengths. In some embodiments, the catheter further comprises a temperature sensor, the temperature sensor being integral to the distal tip of the electrode. In some embodiments the catheter further comprises one or more ultrasound transducers, the ultrasound transducers being located in the distal section of the catheter, and preferably in the tip of the distal electrode. The ultrasonic transducers are adapted to assess a tissue thickness either below or adjacent to the catheter tip. In some embodiments, the catheter comprises multiple transducers adapted to provide depth information covering a situation where the catheter tip is relatively perpendicular to a myocardium or relatively parallel to a myocardium.

In some embodiments the catheter further comprises an irrigation means for the purposes of flushing catheter openings with an irrigation fluid to clear the tip of blood, cooling a tissue-electrode interface, preventing a thrombus formation, and dispersing an RF energy to a greater zone of tissue, thus forming larger lesions than non-irrigated catheters. In some embodiments, the irrigating fluid is maintained within the catheter tip at a positive pressure relative to outside of the tip, and is adapted for continuous flushing of the openings.

In some embodiments, the catheter further comprises an electromagnetic location sensor adapted for locating and navigating the catheter. In some embodiments, the electromagnetic location sensor is adapted to locate the tip of the catheter in a navigation system of any one of several catheter manufacturers. The sensor picks up electromagnetic energy from a source location and computes location through triangulation or other means. In some embodiments the catheter comprises more than one transducer adapted to render a position of the catheter body and a curvature of the catheter body on a navigation system display.

In some embodiments, a catheter adapted to ablate tissue comprises a catheter body, and a tip electrode adapted to ablate a tissue. In some embodiments the catheter further comprises at least one optical waveguide adapted to deliver light energy to the tissue, and one or more optical waveguides adapted to receive light energy from the tissue. In some embodiments, the catheter further comprises a single optical waveguide adapted to deliver light energy to the tissue and receive light energy from the tissue.

In some embodiments, the catheter is adapted for an ablation energy, the ablation energy being one or more of RF energy, cryo energy, laser, chemical, electroporation, high intensity focused ultrasound or ultrasound, and microwave.

In some embodiments, the tip of the catheter comprises a first electrode adapted for sensing electrical activity of the tissue, a second electrode adapted for transmitting or conducting ablation energy or chemical, a light directing member to direct a light in one or more directions simultaneously, one or more openings for the transmission and receiving of light energy, one or more openings for an irrigation fluid to flow from the tip, and one or more openings adapted for transmitting and receiving light as well as concomitantly flowing irrigation fluid from the tip. In some embodiments the tip of the catheter comprises an electrically conductive material, adapted to allow the first electrode to sense the electrical activity of the tissue in contact with the catheter. In some embodiments, the tip further comprises an electrode adapted for transmitting or conducting ablation energy or a chemical energy. In some embodiments, the tip is adapted to conduct RF energy to the adjacent tissue. In some embodiments, the tip comprises an optically transparent material allowing conduction of laser ablation energy to the adjacent tissue. In some embodiments, the tip comprises a plurality of holes adapted to transmit a chemical used to alter cells of the tissue or of a tissue in close proximity to the tip. In some embodiments, the openings for transmitting and receiving light are in the distal tip. In some embodiments, the tip comprises additional holes adapted to cool the tip with a fluid during an application of ablation energy.

In some embodiments, the tip further comprises at least one opening adapted to allow a directed light energy to illuminate the tissue, and to allow the light energy to return from the tissue to the catheter. In some embodiments, the tip comprises at least one opening in the distal tip for illuminating a tissue along a longitudinal axis of the catheter. In some embodiments, the light energy is directed in a manner that is dependent upon a light directing member having a central lumen allowing a portion of the light to be directed in a longitudinal direction. In some embodiments, the tip further comprises at least one opening in the distal tip for illuminating the tissue in a radial axis with respect to the catheter. In some embodiments, the tip is adapted to direct the light by splitting the primary light source into specific multiple beams using the light directing member.

In some embodiments, the primary light source is a laser, the laser adapted to send a light beam down an optical fiber to the light directing member, wherein the light beam is sent in one or more directions, including straight ahead relative to the tip, to make sure a structure adjacent to the catheter is illuminated. In some embodiments, a structure that is illuminated will transmit optical energy back to the catheter tip and to the light directing member, which in turn reflects the returned light back up the fiber to a spectrometer.

In some embodiments, the tip is configured to direct the light energy independent of any polishing of the interior of the illumination cavity. In some embodiments, the directing of light energy does not depend on the use of an interior wall of the illumination cavity.

In some embodiments, a catheter adapted to support fNADH comprising one or more ultrasound transducers. In some embodiments, the catheter is adapted to measure a wall thickness of an area of interest. In some embodiments, the catheter is adapted to assess a metabolic state of the tissue throughout the wall thickness. In some embodiments, the catheter further comprises ultrasonic transducers adapted to measure cardiac wall thickness and adapted to assess a metabolic state of the myocardium during an application of an RF energy. In some embodiments, the catheter is adapted to identify any metabolically active tissue for the purposes of identifying electrical gaps in lesions.

In some embodiments, the catheter comprises a light-directing component adapted to send light in one or more radial directions and axially simultaneously. In some embodiments, the catheter further comprises a separate or a modular component of the tip electrode, wherein an light directing member is integrated into the tip of the electrode during. In some embodiments, the light directing member has a centrally located lumen for light to pass in the axial direction. In some embodiments, the light directing member is keyed to facilitate alignment of a facet of the light directing member to openings of the catheter tip permitting a transfer of light energy. In some embodiments, the light directing member is integrated into the catheter tip via a snap-fitting, welding, soldering, or gluing into a keyed position in the catheter tip.

In some embodiments, the light directing member is keyed to facilitate a correct alignment of one or more reflecting facets and one or more light ports in the tip of the catheter. In some embodiments, the light directing member is a separate component that is oriented into the catheter tip, adapted to provide a light path through the tip, inline with a longitudinal axis of the catheter. In some embodiments, the light directing member protrudes through the tip and can be welded on the distal side of the tip so that the welding does not interfere or damage a reflective surface of the light directing member. In some embodiments, the light directing member comprises polished stainless steel. In some embodiments, the light directing member comprises platinum or platinum alloys, a material identical to the tip, any material with a reflective surface capable of reflecting or splitting light, or a material that does not fluoresce when illuminated from about 310 nm to about 370 nm. In some embodiments, the light directing member is larger than any aperture of the tip electrode to ensure the light directing member cannot escape through said aperture.

In some embodiments, the light directing member may be optimized to provide the optimum number of facets and the optimum optical path for efficiency. These attributes can be traded off against the desired radial coverage. For example, in connection with tissue contact with the distal tip parallel to the myocardial surface, the radial coverage can be designed so that at least one opening in the side wall of the distal tip is pointed at the myocardium when the tip is parallel to the heart tissue. Likewise, the opening in the front wall of the distal tip may ensure that light is both transmitted and received when the catheter tip is more or less orthogonal to the myocardial surface. In some embodiments, the light directing member is provided with 3 to 4 facets.

In some embodiments, a catheter of the present disclosure comprises of a catheter body with the following components: a catheter with a distal tip positioned at a distal end of the catheter body, the distal tip defining a light chamber, the distal tip having one or more openings for exchange of light energy between the light chamber and tissue, and a the same catheter with a light directing member disposed within the light chamber, the light directing member being configured to direct the light energy to and from the tissue through the one or more openings in the distal tip. In some embodiments, the catheter comprises of one or more optical waveguides extending into the light chamber to deliver light to and from the light chamber. In some embodiments, the catheter has a light directing member and the one or more openings are configured to enable illumination of tissue in the radial and the axial directions. In some embodiments, the catheter has a distal tip that has a dome shaped front wall and straight side walls. In some embodiments, the catheter has one or more openings that are disposed along sidewalls of the distal tip. In some embodiments, the catheter has one or more openings that are disposed circumferentially along the distal tip. In some embodiments, the catheter has one or more openings that are provided in multiple rows along side walls of the distal tip. In some embodiments, the catheter has a distal tip that is comprised of a tissue ablation electrode. In some embodiments, the catheter has a light directing member that is configured to direct light radially through the one or more openings. In some embodiments, the catheter has a light directing member that is comprised of multiple facets. In some embodiments, the catheter has a light directing member that is comprised of multiple facets, wherein the facets are equally spaced. In some embodiments, the catheter has a light directing member that is comprised of multiple facets, wherein the number of the facets corresponds to the number of the openings along side walls of the distal tip. In some embodiments, the catheter has a light directing member that is shaped to reflect the light energy at an angle relative to the longitudinal axis of the catheter.

In some embodiments, the catheter has a light directing member that is comprised of a single-faceted mirror. In some embodiments, the catheter has a light directing member that is rotatable with respect to the light chamber. In some embodiments, the catheter has a light directing member that is comprised of one or more through-holes and the distal tip is comprised of one or more openings disposed on a front wall of the distal tip to enable passage of light in longitudinal direction through the light directing member and the one or more openings of the front wall.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

What is claimed is:

1. A catheter for visualizing ablated tissue comprising:
a catheter body;
a distal tip positioned at a distal end of the catheter body, the distal tip defining an illumination cavity, the distal tip having one or more openings for exchange of light energy between the illumination cavity and tissue;
a light directing member having a plurality of facets being adjacent to one another and being angled with respect to one another to form a front face and disposed within the illumination cavity, the plurality of facets of the light directing member being spaced away from the one or more openings to reflect the light energy to and from the tissue through the one or more openings in the distal tip.

2. The catheter of claim 1, further comprising one or more optical fibers extending into the illumination cavity to deliver the light energy to and from the illumination cavity.

3. The catheter of claim 1, wherein the distal tip further comprises a fiber aligner configured to align the one or more optical fibers with a central axis of the light directing member.

4. The catheter of claim 1, wherein the light directing member and the one or more openings are configured to enable illumination of the tissue by the light energy in a radial direction and an axial direction with respect to a longitudinal axis of the catheter.

5. The catheter of claim 1, wherein the one or more openings are disposed along side walls of the distal tip and the light directing member is shaped to direct the light energy at an angle relative to the longitudinal axis of the catheter through the one or more openings.

6. The catheter of claim 5, wherein the light directing member comprises one or more through-holes and the distal tip comprises one or more openings disposed on a front wall of the distal tip to enable passage of the light energy in longitudinal direction through the light directing member and the one or more openings of the front wall.

7. The catheter of claim 5, wherein the light directing member is aligned with the one or more openings to reflect light only through the one or more openings.

8. The catheter of claim 1, wherein the one or more openings are disposed circumferentially along the distal tip and are spaced apart from one another by equal distance and the plurality of facets of the light directing member are equally spaced and are in alignment with the one or more openings.

9. The catheter of claim 1, wherein the distal tip is configured to deliver ablation energy to the tissue, the ablation energy being selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

10. The catheter of claim 1, further comprising an ultrasound transducer.

11. A system for visualizing ablated tissue comprising:
a catheter comprising a catheter body; a distal tip positioned at a distal end of the catheter body, the distal tip defining a illumination cavity, the distal tip having one or more openings for exchange of light energy between the illumination cavity and tissue; a light directing member having a plurality of facets being adjacent to one another and being angled with respect to one another to form a front face and disposed within the illumination cavity, the plurality of facets of the light directing member being spaced away from the one or more openings to reflect the light energy to and from the tissue through the one or more openings in the distal tip;
a light source;
a light measuring instrument; and
one or more optical fibers in communication with the light source and the light measuring instrument and extending through the catheter body into the illumination cavity of the distal tip, wherein the one or more optical fibers are configured to pass light energy from the light source to the light directing member for illuminating tissue outside the distal tip and the one or more optical fibers are configured to relay light energy reflected from the tissue to the light measuring instrument.

12. The system of claim 11, wherein the distal tip further comprises a fiber aligner configured to align the one or more optical fibers with a central axis of the light directing member.

13. The system of claim 11, wherein the light directing member and the one or more openings are configured to enable illumination of the tissue by the light energy in a radial direction and an axial direction with respect to a longitudinal axis of the catheter.

14. The system of claim 11, wherein the one or more openings are disposed along side walls of the distal tip and the light directing member is shaped to reflect the light energy at an angle relative to the longitudinal axis of the catheter through the one or more openings.

15. The system of claim 14, wherein the light directing member comprises one or more through-holes and the distal tip comprises one or more openings disposed on a front wall of the distal tip to enable passage of the light energy in longitudinal direction through the light directing member and the one or more openings of the front wall.

16. The system of claim 11, wherein the one or more openings are disposed circumferentially along the distal tip and are spaced apart from one another by equal distance and the plurality of facets of the light directing member are equally spaced facets in alignment with the one or more openings.

17. The system of claim 11, further comprising an ultrasound transducer.

18. The system of claim 11, further comprising a source of ablation energy in communication with the distal tip to deliver ablation energy to the tissue, the ablation energy being selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

19. A method for visualizing ablated tissue comprising:
advancing a catheter to a cardiac tissue in need of ablation, the catheter comprising a catheter body; a distal tip positioned at a distal end of the catheter body, the distal tip defining a illumination cavity, the distal tip having one or more openings for exchange of light between the illumination cavity and tissue; a light directing member having a plurality of facets being adjacent to one another and being angled with respect to one another to form a front face and disposed within the illumination cavity, the plurality of facets of the light directing member being spaced away from the one or more openings to reflect the light to and from the tissue through the one or more openings in the distal tip;
causing the light directing member to direct light through the one or more openings in the distal tip of the catheter to excite nicotinamide adenine dinucleotide hydrogen (NADH) in an area of the cardiac tissue including ablated cardiac tissue and non-ablated cardiac tissue;
collecting light reflected from the cardiac tissue through the one or more openings and directing the collected light to a light measuring instrument;
imaging the area of the cardiac tissue to detect NADH fluorescence of the area of the cardiac tissue; and
producing a display of the imaged, illuminated cardiac tissue, the display illustrating the ablated cardiac tissue as having less fluorescence than non-ablated cardiac tissue.

20. The method of claim 19, further comprising ablating tissue with the distal tip prior to imaging the tissue.

21. The method of claim 19, further comprising ablating additional non-ablated cardiac tissue identified by distinguishing between the ablated cardiac tissue and the non-ablated cardiac tissue based on the amount of fluorescence.

22. The system of claim 19, wherein the light directing member and the one or more openings are configured to enable illumination of the cardiac tissue in a radial direction and an axial direction with respect to a longitudinal axis of the catheter.

* * * * *